(12) United States Patent
Savage et al.

(10) Patent No.: US 9,931,350 B2
(45) Date of Patent: *Apr. 3, 2018

(54) ANTI-INFECTIVE AND OSTEOGENIC COMPOSITIONS AND METHODS OF USE

(71) Applicants: Paul B. Savage, Mapleton, UT (US); Carl Genberg, Las Vegas, NV (US)

(72) Inventors: Paul B. Savage, Mapleton, UT (US); Carl Genberg, Las Vegas, NV (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/645,040

(22) Filed: Mar. 11, 2015

(65) Prior Publication Data

US 2015/0258123 A1 Sep. 17, 2015

Related U.S. Application Data

(60) Provisional application No. 61/953,176, filed on Mar. 14, 2014.

(51) Int. Cl.
| | | |
|---|---|---|
| *A01N 45/00* | (2006.01) |
| *A61K 31/56* | (2006.01) |
| *A61K 31/575* | (2006.01) |
| *A61K 45/06* | (2006.01) |

(52) U.S. Cl.
CPC ............ *A61K 31/575* (2013.01); *A61K 45/06* (2013.01)

(58) Field of Classification Search
None
See application file for complete search history.

(56) References Cited

U.S. PATENT DOCUMENTS

| | | |
|---|---|---|
| 4,248,236 A | 2/1981 | Linder |
| 4,661,341 A | 4/1987 | Benedict et al. |
| 4,723,950 A | 2/1988 | Lee |
| 4,765,855 A | 8/1988 | Geoffroy-Dechaume et al. |
| 4,842,593 A | 6/1989 | Jordan et al. |
| 4,972,848 A | 11/1990 | DiDomenico |
| 5,025,754 A | 6/1991 | Plyler |
| 5,286,479 A | 2/1994 | Garlich et al. |
| 5,310,545 A | 5/1994 | Eisen |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,721,359 A | 2/1998 | Dunn et al. |
| 6,117,332 A | 9/2000 | Hatch et al. |
| 6,228,393 B1 | 5/2001 | DiCosmo et al. |
| 6,329,488 B1 | 12/2001 | Terry et al. |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,803,066 B2 | 10/2004 | Traeder et al. |
| 6,872,303 B2 | 3/2005 | Knapp et al. |
| 6,939,376 B2 | 9/2005 | Shulze et al. |
| 7,282,214 B2 | 10/2007 | Wilcox et al. |
| 7,381,439 B2 | 6/2008 | Hilgren et al. |
| 7,598,234 B2 | 10/2009 | Savage et al. |
| 7,659,061 B2 | 2/2010 | Hendl et al. |
| 7,754,705 B2 * | 7/2010 | Savage .................. A61K 31/56 514/169 |
| 7,854,941 B2 | 12/2010 | Urban et al. |
| 7,993,903 B2 | 8/2011 | Hayakawa et al. |
| 8,211,879 B2 | 7/2012 | Savage et al. |
| 8,529,681 B1 | 9/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 9,155,746 B2 * | 10/2015 | Genberg ............ A61K 38/1875 |
| 9,161,942 B2 * | 10/2015 | Genberg ............ A61K 31/575 |
| 9,527,883 B2 | 12/2016 | Savage et al. |
| 2002/0091278 A1 | 7/2002 | Savage et al. |
| 2003/0018306 A1 | 1/2003 | Bucay-Couto et al. |
| 2003/0099717 A1 | 5/2003 | Cabrera |
| 2004/0009227 A1 | 1/2004 | Yao |
| 2004/0018154 A1 | 1/2004 | Pan |
| 2004/0058974 A1 | 3/2004 | Courtney et al. |

(Continued)

FOREIGN PATENT DOCUMENTS

| | | |
|---|---|---|
| CN | 101378761 | 3/2009 |
| CN | 102172356 | 9/2011 |

(Continued)

OTHER PUBLICATIONS

Williams et al., "In vivo efficacy of a silicone-cationic steroid antimicrobial coating to prevent implant-related infection," Biomaterials. Nov. 2012; 33(33): 8641-8656 (Department of Brigham Young University).*
Schmidmaier, "Local application of growth factors (insulin-like growth factor-1 and transforming growth factor-β1) from a biodegradable poly(D,L-lactide) coating of osteosynthetic implants accelerates fracture healing in rats," Bone vol. 28. No. 4, Apr. 2001.*
U.S. Appl. No. 14/750,928, filed Jun. 25, 2015, Genberg et al.
U.S. Appl. No. 14/830,356, filed Aug. 19, 2015, Savage.
U.S. Appl. No. 14/842,582, filed Sep. 1, 2015, Genberg et al.
U.S. Appl. No. 14/848,819, filed Sep. 9, 2015, Genberg et al.
U.S. Appl. No. 14/866,213, filed Sep. 25, 2015, Savage.
U.S. Appl. No. 14/873,013, filed Oct. 1, 2015, Savage et al.

(Continued)

*Primary Examiner* — Jared D Barsky
(74) *Attorney, Agent, or Firm* — Workman Nydegger

(57) ABSTRACT

Cationic steroidal antimicrobials ("CSAs" or "ceragenins") and methods of making and using the same. Particularly advantageous uses include treating infections in patient and sub-patient populations, especially those having a bone disease, a broken bone, a bone infection, or a bone implant.

28 Claims, 5 Drawing Sheets

(56) References Cited

U.S. PATENT DOCUMENTS

| | | |
|---|---|---|
| 2004/0071781 A1 | 4/2004 | Chattopadhyay et al. |
| 2004/0170563 A1 | 9/2004 | Meade et al. |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0062742 A1 | 3/2006 | Davis et al. |
| 2006/0269485 A1 | 11/2006 | Friedman et al. |
| 2007/0106393 A1 | 5/2007 | Miles et al. |
| 2007/0134292 A1 | 6/2007 | Suokas et al. |
| 2007/0190066 A1 | 8/2007 | Savage et al. |
| 2007/0190067 A1 | 8/2007 | Savage et al. |
| 2007/0190558 A1 | 8/2007 | Savage et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0252781 A1 | 10/2009 | Sawhney et al. |
| 2009/0324517 A1 | 12/2009 | Kline |
| 2010/0092398 A1 | 4/2010 | Reynolds |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0091376 A1 | 4/2011 | Savage |
| 2011/0123624 A1 | 5/2011 | Zasloff |
| 2011/0135742 A1 | 6/2011 | Kim et al. |
| 2012/0088733 A1 | 4/2012 | Kim et al. |
| 2012/0107382 A1 | 5/2012 | Savage et al. |
| 2013/0022651 A1 | 1/2013 | Savage |
| 2013/0053507 A1 | 2/2013 | Savage |
| 2013/0234842 A1 | 9/2013 | Genberg et al. |
| 2013/0236619 A1 | 9/2013 | Savage |
| 2013/0243823 A1 | 9/2013 | Genberg et al. |
| 2013/0243840 A1 | 9/2013 | Savage et al. |
| 2013/0245760 A1 | 9/2013 | Savage et al. |
| 2013/0280312 A1 | 10/2013 | De Szalay |
| 2013/0280391 A1 | 10/2013 | Savage |
| 2014/0107090 A1 | 4/2014 | Beus et al. |
| 2014/0194401 A1 | 7/2014 | Genberg et al. |
| 2014/0219914 A1 | 8/2014 | Govindan et al. |
| 2014/0271761 A1 | 9/2014 | Savage et al. |
| 2014/0274913 A1 | 9/2014 | Savage et al. |
| 2014/0315873 A1 | 10/2014 | Beus et al. |
| 2014/0336131 A1 | 11/2014 | Savage et al. |
| 2014/0363780 A1 | 12/2014 | Vazquez et al. |
| 2014/0369941 A1 | 12/2014 | Vazquez et al. |
| 2015/0093423 A1 | 4/2015 | Savage et al. |
| 2015/0110767 A1 | 4/2015 | Savage et al. |
| 2016/0193232 A1 | 3/2016 | Beus et al. |
| 2016/0199390 A1 | 3/2016 | Beus et al. |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1 | 5/2017 | Savage |
| 2017/0210776 A1 | 7/2017 | Savage |
| 2017/0232004 A1 | 8/2017 | Savage et al. |
| 2017/0258963 A1 | 9/2017 | Savage et al. |

FOREIGN PATENT DOCUMENTS

| | | |
|---|---|---|
| EP | EP 0341951 | 11/1989 |
| EP | 1208844 | 5/2002 |
| EP | 1219631 | 7/2002 |
| JP | 02014741 | 1/1990 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004506645 | 3/2004 |
| JP | 2010533051 | 10/2010 |
| JP | 2010538074 | 12/2010 |
| JP | 2011527702 | 11/2011 |
| JP | 2014500741 | 1/2014 |
| WO | WO 1995024415 | 9/1995 |
| WO | WO9827106 | 6/1998 |
| WO | WO 1999044616 | 9/1999 |
| WO | WO 2000042058 | 7/2000 |
| WO | WO 2002014342 | 2/2002 |
| WO | WO2002067979 | 9/2002 |
| WO | WO 2003015757 | 2/2003 |
| WO | WO 03090799 | 11/2003 |
| WO | WO2004082588 | 9/2004 |
| WO | WO 2004112852 | 12/2004 |
| WO | WO 2007089903 | 8/2007 |
| WO | WO 2007089906 | 8/2007 |
| WO | WO 2007089907 | 8/2007 |
| WO | WO 2007134176 | 11/2007 |
| WO | WO 2008038965 | 4/2009 |
| WO | WO 2009079066 | 6/2009 |
| WO | WO2009144708 | 12/2009 |
| WO | WO2010006192 | 1/2010 |
| WO | WO 2010036427 | 4/2010 |
| WO | WO 2010062562 | 6/2010 |
| WO | WO2011066260 | 6/2011 |
| WO | WO 2011109704 | 9/2011 |
| WO | WO 2012061651 | 5/2012 |
| WO | WO 2013029055 | 2/2013 |
| WO | WO 2013029059 | 2/2013 |
| WO | WO 2013109236 | 7/2013 |

OTHER PUBLICATIONS

U.S. Appl. No. 14/875,953, filed Oct. 6, 2015, Savage.
U.S. Appl. No. 14/926,738, filed Oct. 29, 2015, Vazquez et al.
Berge et al., "Pharmaceutical Salts", Journal of Pharmaceutical Sciences, Jan. 1977, vol. 66, No. 1, pp. 1-19.
Clara et al., "Preclinical evaluation of magainin-A as a contraceptive antimicrobial agent", Fertility and Sterility 81 (5), pp. 1357-1365, 2004.
International Search Report for PCT Application No. PCT/US2014/034986 dated Aug. 28, 2014.
International Search Report for PCT Application No. PCT/US2013/065510, dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).
Zanger et al., "Structure-Activity Relationship and Drug Design", Remington's Pharmaceutical Sciences, Chapter 27, 16th Edition, 1980, pp. 420-425.
U.S. Appl. No. 13/783,007, filed Mar. 1, 2013, Savage.
U.S. Appl. No. 14/364,283, filed Jul. 29, 2014, Vazquez et al.
U.S. Appl. No. 14/602,499, filed Jan. 22, 2015, Savage.
U.S. Appl. No. 14/602,071, filed Jan. 21, 2015, Savage.
U.S. Appl. No. 14/624,200, filed Feb. 17, 2015, Savage.
U.S. Appl. No. 14/642,905, filed Mar. 10, 2015, Beus et al.
U.S. Appl. No. 14/644,946, filed Mar. 11, 2015, Beus et al.
U.S. Appl. No. 14/694,028, filed Apr. 23, 2015, Beus et al.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.

(56) References Cited

OTHER PUBLICATIONS

Britton et al, "Imaging bacterial infection with 99mTc-ciprofloxacin (Infection)", Journal of Clinical Pathology, vol. 55, pp. 817-823, Apr. 6, 2015.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Chin et al, "Antimicrobial Activities of Ceragenins against Clinicial Isolates of Resistant *Staphylococcus aureas*.", Antimcirobial Agents and Chemotherapy, vol. 51, No. 4, Apr. 2007, p. 1268-1273.
Li Chunhong, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Ding, et al., "Origins of cell selectivity of cationic steroid antibiotics", Journal of American Chemical Society, Oct. 2004, pp. 13642-13648.
Fritsch et al, "In Vitro Activity of Nine Developmental Cationic Steroid Compounds (Ceragenins) against Clnical Isolates of Clostridium difficile", The 46th Interscience Conference on Antimicrobial Agents and Chemotherapy, Sep. 27, 2006, pp. 1-1.
Qunying Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Qunying Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/o10062704/suppl file/o10062704 sl.pdf.
Michael D. Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
International Search Report for PCT Application No. PCT/US2009/047485 dated Feb. 17, 2010.
International Search Report for PCT Application No. PCT/US2011/059225 dated Jan. 31, 2012.
International Search Report for PCT Application No. PCT/US2012/047750, dated Oct. 5, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
Lai, et al., "Controlled Released of a Bactericidal Ceragenin-Polymer Conjugate", Sep. 27, 2006, p. 1, 46th Annual Interscience Conference on Antimicrobial Agents and Chemotherapy.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.
Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.
Savage, et al., "Antibacterial Activities of Thin Films Containing Ceragenins", Microbial Surfaces: Structure, Interactions and Reactivity, ACS, May 30, 2008, pp. 65-78.
Paul B. Savage, et al: "Antibacterial Properties of cationic steroid antibiotics", FEMS Microbiology Letters, vol. 217, Nov. 2002, pp. 1-7.
P. B. Savage, et al., "Thin Films Containing Ceragenins Prevent Biofilm Formation on Endotracheal Tubes", 9th International Federation of Infection Control Congress, Oct. 14, 2008, pp. 1-1.
P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.
K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.
Steeneveld, et al., "Cow-specific treatment of clinical mastitis: an economic approach", Journal of Dairy Science vol. 94, Jan. 2011, pp. 174-188.
Suzuki et al., "Molecular Genetics of Plant Sterol Backbone Synthesis", 2007; Lipids; 42: 47-54.
Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.
Melinda Yin, et al., "Antiangiogenic Treatment Delays Chondrocyte Maturation and Cone Formation During Lim Skeltogenesis", Journal of Vone and Mineral Research, American Society for Bone and Mineral Research, New York, NY, US, vol. 17, No. 1, Jan. 1, 2002.
U.S. Appl. No. 13/554,957, filed Jul. 20, 2012, Office Action dated Apr. 1, 2014.
U.S. Appl. No. 13/554,957, filed Jul. 20, 2012, Notice of Allowance dated Aug. 1, 2014.
U.S. Appl. No. 13/594,608, filed Aug. 24, 2012, Office Action dated Jan. 30, 2014.
U.S. Appl. No. 13/594,612, filed Aug. 24, 2012, Office Action dated May 15, 2014.
U.S. Appl. No. 13/615,324, filed Sep. 13, 2012, Office Action dated Jan. 30, 2014.
U.S. Appl. No. 13/554,930, filed Jul. 20, 2012, Office Action dated Jul. 11, 2014.
U.S. Appl. No. 13/783,131, filed Mar. 1, 2013, Office Action dated Oct. 23 ,2014.
U.S. Appl. No. 13/000,010, filed Jun. 16, 2009, Restriction Requirement dated Dec. 4, 2012.
U.S. Appl. No. 13/288,902, filed Jun. 21, 2012, Restriction Requirement dated Jun. 21, 2012.
U.S. Appl. No. 13/288,902, filed Jun. 21, 2012, Office Action dated Nov. 7, 2012.
U.S. Appl. No. 13/288,902, filed Jun. 21, 2012, Notice of Allowance dated Aug. 9, 2013.
U.S. Appl. No. 13/288,892, filed Nov. 3, 2011, Restriction Requirement dated Dec. 10, 2012.
U.S. Appl. No. 13/288,892, filed Nov. 3, 2011, Office Action dated May 9, 2013.
U.S. Appl. No. 13/288,892, filed Nov. 3, 2011, Notice of Allowance dated Nov. 29, 2013.
U.S. Appl. No. 14/056,122, filed Oct. 17, 2013, Office Action dated Sep. 3, 2014.
U.S. Appl. No. 13/615,244, filed Sep. 13, 2012, Office Action dated Jan. 16, 2015.
U.S. Appl. No. 14/257,776, filed Apr. 21, 2014, Restriction Requirement dated Jan. 22, 2015.
U.S. Appl. No. 14/364,283, filed Jul. 29, 2014, Office Action dated Feb. 11, 2015.
U.S. Appl. No. 14/339,342, filed Jul. 23, 2014, Office Action dated Mar. 5, 2015.
U.S. Appl. No. 13/554,930, filed Jul. 20, 2012, Final Office Action dated Mar. 16, 2015.

(56) References Cited

OTHER PUBLICATIONS

U.S. Appl. No. 13/783,007, filed Mar. 1, 2013, Restriction Requirement dated Mar. 31, 2015.
U.S. Appl. No. 13/000,010, filed Dec. 17, 2010, Office Action dated Apr. 14, 2015.
U.S. Appl. No. 14/257,776, filed Apr. 21, 2014, Office Action dated Apr. 16, 2015.
U.S. Appl. No. 13/841,549, filed Mar. 15, 2013, Office Action dated Apr. 23, 2015.
Bush, "Staphylococcal Infections", Merck Manuals Professional Edition, http://www.merckmanuals.com/professional/infectious-diseases/gram-positive-cocci/staphylococcal-infections.
Cipolla et al., "Inhaled antibiotics to treat lung infection", Pharm Pat Anal., Sep. 2013.
Elder et al., "The Utility of Sulfonate Salts in Drug Development", Journal of Pharmaceutical Sciences 99(7): 2948-2961.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Louw et al., "Recueil des Travaux Chimiques des Pays-Bas et la Belgique", vol. 73, pp. 667-676, 1954.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, CO—Published Dec. 20, 2007).
Pycock, "The Dirty Mare", https://www.equine-reproduction.com/articles/DirtyMare.shtml, 2003.

* cited by examiner

ANTI-INFECTIVE AND OSTEOGENIC COMPOSITIONS AND METHODS OF USE

CROSS-REFERENCE TO RELATED APPLICATIONS

This application claims the benefit of U.S. Provisional Application No. 61/953,176 filed Mar. 14, 2014, the disclosure of which is incorporated herein in its entirety.

BACKGROUND

1. Field of the Invention

The present application relates to pharmaceutical chemistry, biochemistry, and medicine, more particularly, cationic steroidal antimicrobial ("CSA") compounds (or "ceragenins") and CSA compositions.

2. Description of the Related Art

Endogenous antimicrobial peptides, such as the human cathelicidin LL-37, play key roles in innate immunity. LL-37 is found in airway mucus and is believed to be important in controlling bacterial growth in the lung. Antimicrobial peptides are found in organisms ranging from mammals to amphibians to insects to plants. The ubiquity of antimicrobial peptides has been used as evidence that these compounds do not readily engender bacterial resistance. In addition, considering the varied sequences of antimicrobial peptides among diverse organisms, it is apparent that they have evolved independently multiple times. Thus, antimicrobial peptides appear to be one of "Nature's" primary means of controlling bacterial growth. However, clinical use of antimicrobial peptides presents significant issues, including the relatively high cost of producing peptide-based therapeutics, the susceptibility of peptides to proteases generated by the host and by bacterial pathogens, and deactivation of antimicrobial peptides by proteins and DNA in lung mucosa.

An attractive means of harnessing the antibacterial activities of antimicrobial peptides without the issues delineated above is to develop non-peptide mimics of antimicrobial peptides that display the same broad-spectrum antibacterial activity utilizing the same mechanism of action. Non-peptide mimics would offer lower-cost synthesis and potentially increased stability to proteolytic degradation. In addition, control of water solubility and charge density may be used to control association with proteins and DNA in lung mucosa.

With over 1,600 examples of antimicrobial peptides known, it is possible to categorize the structural features common to them. While the primary sequences of these peptides vary substantially, morphologies adopted by a vast majority are similar. Those that adopt alpha helix conformations juxtapose hydrophobic side chains on one face of the helix with cationic (positively charged) side chains on the opposite side. Similar morphology is found in antimicrobial peptides that form beta sheet structures: hydrophobic side chains on one face of the sheet and cationic side chains on the other.

SUMMARY OF THE INVENTION

Disclosed herein are methods of treating or preventing an infection in a subject in need thereof, comprising administering to the subject a compound of Formula (I), or pharmaceutically acceptable salt thereof:

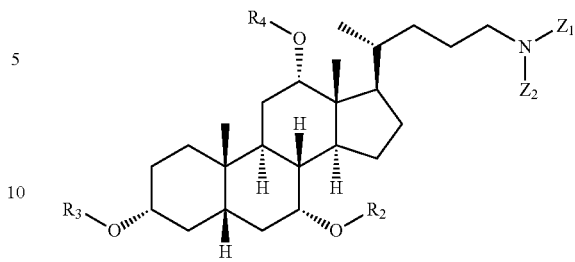

(I)

wherein, $Z_1$ and $Z_2$ are independently selected from the group consisting of optionally substituted alkyl; optionally substituted alkenyl; and optionally substituted alkynyl; or H, with the proviso that $Z_1$ and $Z_2$ are not both H;

$R_2$, $R_3$, and $R_4$ are independently selected from the group consisting of optionally substituted protected or unprotected amino-$C_a$-alkyl; optionally substituted protected or unprotected amino-$C_a$-alkylcarbonyl; and optionally substituted protected or unprotected amino-$C_a$-alkylthiocarbonyl; and a is 2-5. Preferably neither $Z_1$ nor $Z_2$ is H.

In some embodiments, the subject is a vertebrate, and in some cases is a mammal. In some embodiments, the subject is a human. In some embodiments, the subject is in need of osteogenesis and the compound of Formula (I) promotes osteogenesis. In some embodiments, the subject has a bone disease, a broken bone, a bone infection, or a bone implant. In some embodiments, the subject has a bone disease selected from the group consisting of bone resorption, osteoarthritis, osteoporosis, osteomalacia, osteitis fibrosa cystica, osteochondritis dissecans, osteomalacia, osteomyelitis, osteopenia, osteonecrosis, and porotic hyperostosis. In some embodiments, the subject has a broken bone and the broken bone results from a traumatic fracture, a critical sized bone defect, distraction osteogenesis, spine fusion surgery, joint replacement, an orthopaedic implant (bone implant), or a biopsy. In some embodiments, the administration of the compound of Formula (1) treats or prevents a bone disease, a broken bone, a bone infection, or a bone implant.

In some embodiments, the infection is a bacterial infection. In some embodiments, the infection is a drug-resistant bacterial infection. In some embodiments, the infection is a *staphylococcus* or *pseudomonas* bacterial infection, non-limiting examples of which include Methicillin-resistant *Staphylococcus aureus* (MRSA) and Tobramycin-resistant *Pseudomonas aeruginosa* (TRPA). In some embodiments, the infection is a gram negative bacterial infection. In some embodiments, the infection is a bone infection. In some embodiments, the infection is an *S. aureus* or *P. aeruginosa* infection. In some embodiments, $Z_1$ and $Z_2$ are optionally substituted alkyl.

In some embodiments, $Z_1$ and $Z_2$ are optionally substituted alkenyl. In some embodiments, $Z_1$ and $Z_2$ are optionally substituted alkynyl. In some embodiments, $Z_1$ and $Z_2$ are independently selected from the group consisting of optionally substituted $C_1$-$C_{20}$-alkyl; optionally substituted $C_3$-$C_{20}$-alkenyl; and optionally substituted $C_3$-$C_{20}$-alkynyl. In some embodiments, $Z_1$ and $Z_2$ are independently selected from the group consisting of optionally substituted $C_3$-$C_{10}$-alkyl; optionally substituted $C_3$-$C_{10}$-alkenyl; and optionally substituted $C_3$-$C_{10}$-alkynyl. In some embodiments, $Z_1$ and $Z_2$ are independently selected from the group consisting of optionally substituted $C_5$-$C_8$-alkyl; optionally substituted $C_5$-$C_8$-alkenyl; and optionally substituted $C_5$-$C_8$-alkynyl. In some embodiments, $Z_1$ and $Z_2$ are optionally substituted $C_5$-$C_8$-alkyl. In some embodiments, $Z_1$ and $Z_2$ are unsubstituted $C_5$-$C_8$-alkyl.

In some embodiments, $R_2$, $R_3$, and $R_4$, are amino-$C_a$-alkyl or amino-$C_a$-alkylcarbonyl. In some embodiments, $R_2$, $R_3$, and $R_4$, are amino-$C_a$-alkyl. In some embodiments, $R_2$, $R_3$, and $R_4$, are amino-$C_a$-alkylcarbonyl.

In some embodiments, a is 2. In some embodiments, a is 3. In some embodiments, a is 4. In some embodiments, a is 5.

In some embodiments, the protected amino-$C_a$-alkyl and the protected amino-$C_a$-alkylcarbonyl are protected with a group independently selected from Fmoc, Boc, allyl, acetyl, benzyl, or CBz. In some embodiments, $R_2$, $R_3$, and $R_4$, are independently selected from the group consisting of carbamate protected or unprotected amino-$C_a$-alkyl and carbamate protected or unprotected amino-$C_a$-alkylcarbonyl. In some embodiments, $R_2$, $R_3$, and $R_4$, are independently selected from the group consisting of Fmoc protected or unprotected amino-$C_a$-alkyl and Fmoc protected or unprotected amino-$C_a$-alkylcarbonyl. In some embodiments, $R_2$, $R_3$, and $R_4$, are independently selected from the group consisting of Boc protected or unprotected amino-$C_a$-alkyl and Boc protected or unprotected amino-$C_a$-alkylcarbonyl.

In some embodiments the compound of Formula (I) is administered in conjuction with bone morphogenic protein (BMP).

In some embodiments, the compound of Formula (I) is:

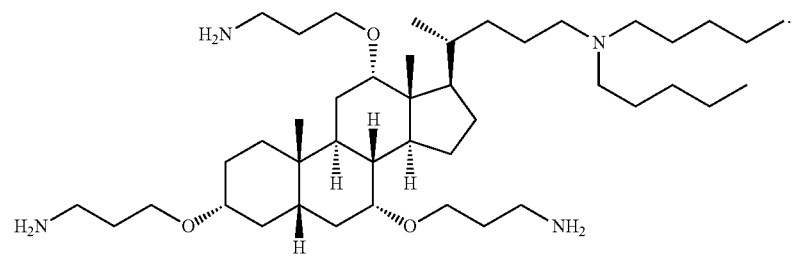

(CSA-90)

In some embodiments, the compound of Formula (I) is:

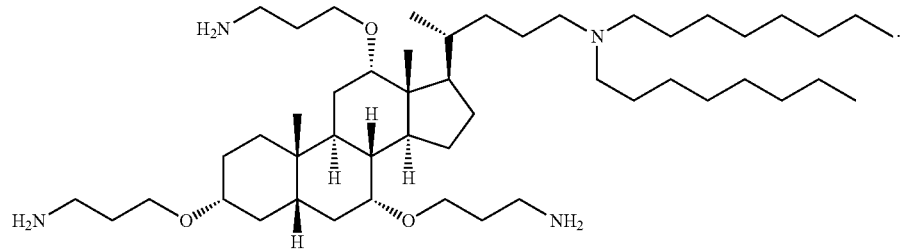

(CSA-91)

In some embodiments, the compound of Formula (I) is:

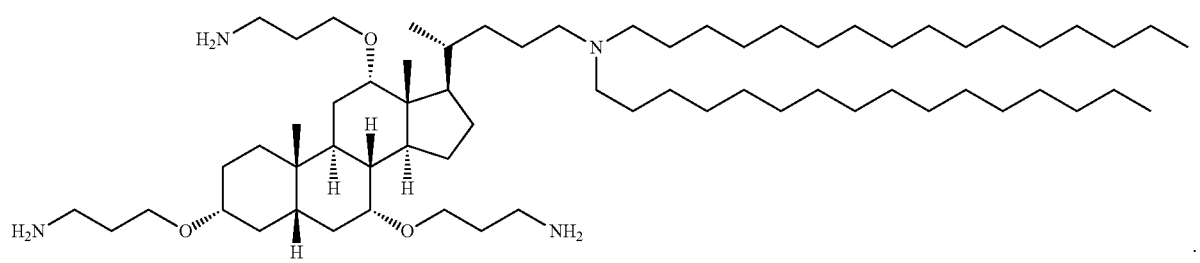

(CSA-133)

In some embodiments, the compound of Formula (I) is:

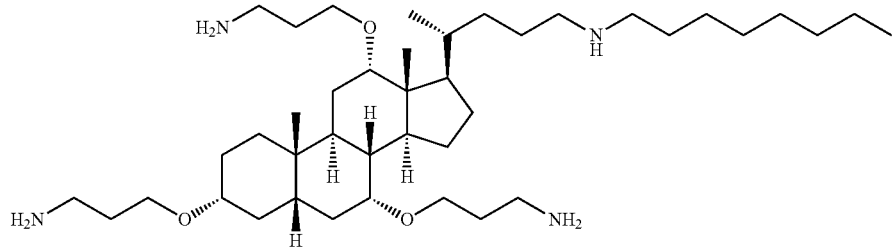

(CSA-13)

In some embodiments, the compound of Formula (I) is not CSA-13.

In some embodiments, the optional substituent is fluorine. In some embodiments, the compound is not optionally substituted.

In some embodiments, the pharmaceutically acceptable salt is a hydrochloride salt.

Additional features and advantages will be set forth in part in the description that follows, and in part will be obvious from the description, or may be learned by practice of the embodiments disclosed herein. The objects and advantages of the embodiments disclosed herein will be realized and attained by means of the elements and combinations particularly pointed out in the appended claims. It is to be understood that both the foregoing brief summary and the following detailed description are exemplary and explanatory only and are not restrictive of the embodiments disclosed herein or as claimed.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION

Figure 1:
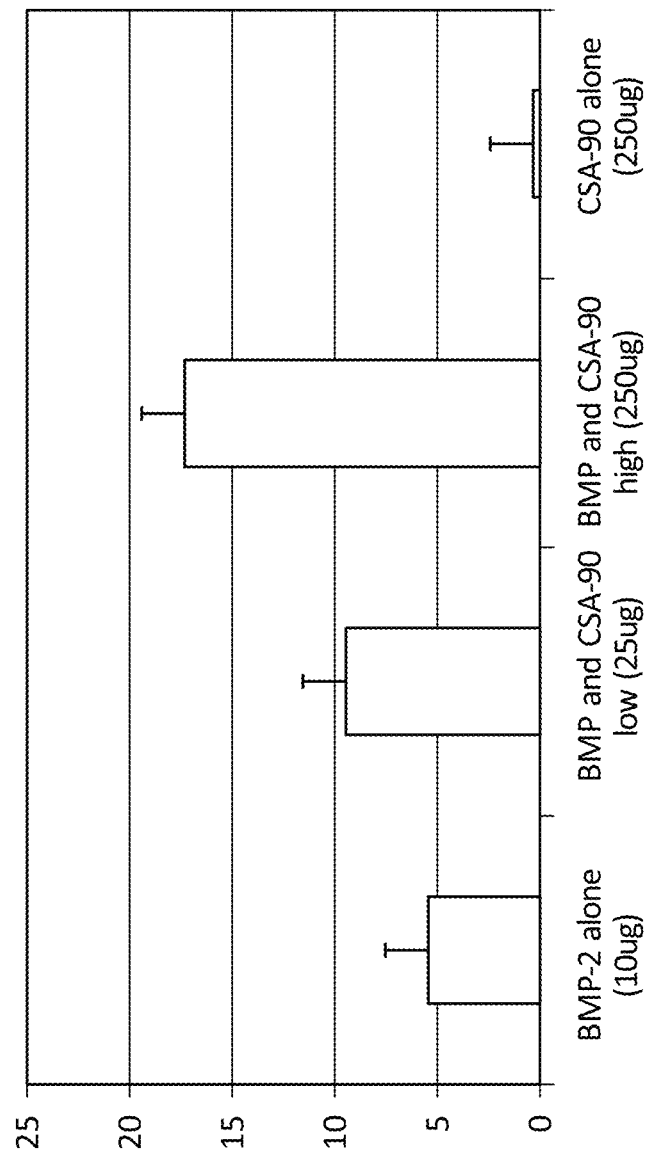
FIG. 1 is a graph showing bone volume by microCT of ectopic bone nodules for various treatments.

The embodiments disclosed herein will now be described by reference to some more detailed embodiments, with occasional reference to any applicable accompanying drawings. These embodiments may, however, be embodied in different forms and should not be construed as limited to the embodiments set forth herein. Rather, these embodiments are provided so that this disclosure will be thorough and complete, and will fully convey the scope of the embodiments to those skilled in the art.

Definitions

Unless otherwise defined, all technical and scientific terms used herein have the same meaning as commonly understood by one of ordinary skill in the art to which these embodiments belong. The terminology used in the description herein is for describing particular embodiments only and is not intended to be limiting of the embodiments. As used in the specification and the appended claims, the singular forms "a," "an," and "the" are intended to include the plural forms as well, unless the context clearly indicates otherwise. All publications, patent applications, patents, and other references mentioned herein are incorporated by reference in their entirety.

Terms and phrases used in this application, and variations thereof, especially in the appended claims, unless otherwise expressly stated, should be construed as open ended as opposed to limiting. As examples of the foregoing, the term "including" should be read to mean "including, without limitation," "including but not limited to," and the like; the term "comprising" as used herein is synonymous with "including," "containing," or "characterized by," and is inclusive or open-ended and does not exclude additional, unrecited elements or method steps; the term "having" should be interpreted as "having at least"; the term "includes" should be interpreted as "includes but is not limited to"; the term "example" is used to provide exemplary instances of the item in discussion, not an exhaustive or limiting list thereof; and use of terms like "preferably," "preferred," "desired," or "desirable," and words of similar meaning should not be understood as implying that certain features are critical, essential, or even important to the structure or function of the invention, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof.

Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present embodiments. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Every numerical range given throughout this specification and claims will include every narrower numerical range that falls within such broader numerical range, as if such narrower numerical ranges were all expressly written herein. Where a range of values is provided, it is understood that the upper and lower limit, and each intervening value between the upper and lower limit of the range is encompassed within the embodiments.

As used herein, the singular forms "a," "and," and "the" include plural referents unless the context clearly indicates otherwise. Thus, for example, reference to "a compound" or "a CSA" includes a plurality of compounds/CSAs and reference to "an infection" can include reference to one or more infections, and so forth.

As used herein, any "R" group(s) such as, without limitation, $R_1$, $R_2$, $R_3$, and $R_4$ represent substituents that can be attached to the indicated atom. Unless otherwise specified, an R group may be substituted or unsubstituted.

As used herein, any "Z" group(s) such as, without limitation, $Z_1$ and $Z_2$ represent substituents that can be attached to the indicated atom. Unless otherwise specified, an R group may be substituted or unsubstituted.

A "ring" as used herein can be heterocyclic or carbocyclic. The term "saturated" used herein refers to a ring having each atom in the ring either hydrogenated or substituted such that the valency of each atom is filled. The term "unsaturated" used herein refers to a ring where the valency of each atom of the ring may not be filled with hydrogen or other substituents. For example, adjacent carbon atoms in the fused ring can be doubly bound to each other. Unsaturation can also include deleting at least one of the following pairs and completing the valency of the ring carbon atoms at these deleted positions with a double bond.

Whenever a group is described as being "optionally substituted" that group may be unsubstituted, or substituted with one, two, three or more of the indicated substituents, which may be the same or different, each replacing a hydrogen atom, unless otherwise indicated. If no substituents are indicated, it is meant that the indicated "substituted" group may be substituted with one or more group(s) individually and independently selected from alkyl, alkenyl, alkynyl, cycloalkyl, cycloalkenyl, cycloalkynyl, acylalkyl, alkoxyalkyl, aminoalkyl, amino acid, aryl, heteroaryl, heteroalicyclyl, aralkyl, heteroaralkyl, (heteroalicyclyl)alkyl, hydroxy, protected hydroxyl, alkoxy, aryloxy, acyl, mercapto, alkylthio, arylthio, cyano, halogen (e.g., F, Cl, Br, and I), thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, oxo, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group, alkylaminoalkyl, dialkylaminoalkyl, di(alkyl)aminoalkyl, cyanato, alkylaminoalkylaminoalkylamino, arylaminoalkyl, aminoalkyloxy, aminoalkyloxyalkyl, aminoalkylcarboxy, aminoalkylaminocarbonyl, aminoalkylcarboxamido, guanidinoalkyloxy, hydroxyalkyl and protected derivatives thereof unless otherwise indicated. The substituent may be attached to the group at more than one attachment point. For example, an aryl group may be substituted with a heteroaryl group at two attachment points to form a fused multicyclic aromatic ring system. Biphenyl and naphthalene are two examples of an aryl group that is substituted with a second aryl group.

As used herein, "alkylthio" refers to the formula —SR wherein R is an alkyl as is defined above, such as "$C_1$-$C_9$ alkylthio" and the like, including but not limited to methylmercapto, ethylmercapto, n-propylmercapto, 1-methylethylmercapto (isopropyl-mercapto), n-butylmercapto, iso-butylmercapto, sec-butylmercapto, tert-butylmercapto, and the like.

A "nitro" group refers to an "—$NO_2$" group.

A "cyanato" group refers to an "—OCN" group.

An "isocyanato" group refers to a "—NCO" group.

A "thiocyanato" group refers to a "—SCN" group.

An "isothiocyanato" group refers to an "—NCS" group.

A "sulfenyl" group refers to an "—S—R" group, which may be substituted or unsubstituted. In some embodiments, R is selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 5-10 membered heterocyclyl, as defined herein.

A "sulfinyl" group refers to an "—S(=O)—R" group, which may be substituted or unsubstituted. In some embodiments, R is selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 5-10 membered heterocyclyl, as defined herein.

A "sulfonyl" group refers to an "—$SO_2$R" group, which may be substituted or unsubstituted. In some embodiments, R is selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 5-10 membered heterocyclyl, as defined herein.

An "S-sulfonamido" group refers to a "—$SO_2NR_AR_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 5-10 membered heterocyclyl, as defined herein.

An "N-sulfonamido" group refers to a "—$N(R_A)SO_2R_B$" group in which $R_A$ and $R_B$ are each independently selected from hydrogen, $C_1$-$C_6$ alkyl, $C_2$-$C_6$ alkenyl, $C_2$-$C_6$ alkynyl, $C_3$-$C_7$ carbocyclyl, $C_6$-$C_{10}$ aryl, 5-10 membered heteroaryl, and 5-10 membered heterocyclyl, as defined herein.

An "O-carbamyl" group refers to a "—OC(=O)NR$_A$R$_B$" group in which R$_A$ and R$_B$ are each independently selected from hydrogen, C$_1$-C$_6$ alkyl, C$_2$-C$_6$ alkenyl, C$_2$-C$_6$ alkynyl, C$_3$-C$_7$ carbocyclyl, C$_6$-C$_{10}$ aryl, 5-10 membered heteroaryl, and 5-10 membered heterocyclyl, as defined herein.

An "N-carbamyl" group refers to an "—N(R$_A$)OC(=O)R$_B$" group in which R$_A$ and R$_B$ are each independently selected from hydrogen, C$_1$-C$_6$ alkyl, C$_2$-C$_6$ alkenyl, C$_2$-C$_6$ alkynyl, C$_3$-C$_7$ carbocyclyl, C$_6$-C$_{10}$ aryl, 5-10 membered heteroaryl, and 5-10 membered heterocyclyl, as defined herein.

An "O-thiocarbamyl" group refers to a "—OC(=S)NR$_A$R$_B$" group in which R$_A$ and R$_B$ are each independently selected from hydrogen, C$_1$-C$_6$ alkyl, C$_2$-C$_6$ alkenyl, C$_2$-C$_6$ alkynyl, C$_3$-C$_7$ carbocyclyl, C$_6$-C$_{10}$ aryl, 5-10 membered heteroaryl, and 5-10 membered heterocyclyl, as defined herein.

An "N-thiocarbamyl" group refers to an "—N(R$_A$)OC(=S)R$_B$" group in which R$_A$ and R$_B$ are each independently selected from hydrogen, C$_1$-C$_6$ alkyl, C$_2$-C$_6$ alkenyl, C$_2$-C$_6$ alkynyl, C$_3$-C$_7$ carbocyclyl, C$_6$-C$_{10}$ aryl, 5-10 membered heteroaryl, and 5-10 membered heterocyclyl, as defined herein.

A "C-amido" group refers to a "—C(=O)NR$_A$R$_B$" group in which R$_A$ and R$_B$ are each independently selected from hydrogen, C$_1$-C$_6$ alkyl, C$_2$-C$_6$ alkenyl, C$_2$-C$_6$ alkynyl, C$_3$-C$_7$ carbocyclyl, C$_6$-C$_{10}$ aryl, 5-10 membered heteroaryl, and 5-10 membered heterocyclyl, as defined herein.

An "N-amido" group refers to a "—N(R$_A$)C(=O)R$_B$" group in which R$_A$ and R$_B$ are each independently selected from hydrogen, C$_1$-C$_6$ alkyl, C$_2$-C$_6$ alkenyl, C$_2$-C$_6$ alkynyl, C$_3$-C$_7$ carbocyclyl, C$_6$-C$_{10}$ aryl, 5-10 membered heteroaryl, and 5-10 membered heterocyclyl, as defined herein.

As used herein, "C$_{zz}$" or "C$_{zz}$ to C$_{zzz}$" or "C$_{zz}$-C$_{zzz}$" in which "zz" and "zzz" are integers refer to the number of carbon atoms in the recited structure, such as an alkyl, alkenyl or alkynyl group, or the number of carbon atoms in the ring of a cycloalkyl, cycloalkenyl, cycloalkynyl, aryl, heteroaryl or heteroalicyclyl group. That is, the alkyl, alkenyl, alkynyl, ring of the cycloalkyl, ring of the cycloalkenyl, ring of the cycloalkynyl, ring of the aryl, ring of the heteroaryl or ring of the heteroalicyclyl can contain from "zz" to "zzz", inclusive, carbon atoms. Thus, for example, a "C$_1$ to C$_4$ alkyl" group refers to all alkyl groups having from 1 to 4 carbons, that is, CH$_3$—, CH$_3$CH$_2$—, CH$_3$CH$_2$CH$_2$—, (CH$_3$)$_2$CH—, CH$_3$CH$_2$CH$_2$CH$_2$—, CH$_3$CH$_2$CH(CH$_3$)— and (CH$_3$)$_3$C—. If no "zz" and "zzz" are designated with regard to an alkyl, alkenyl, alkynyl, cycloalkyl cycloalkenyl, cycloalkynyl, aryl, heteroaryl or heteroalicyclyl group, the broadest range described in these definitions is to be assumed.

Unless otherwise specified, as used herein, "alkyl" refers to a straight or branched hydrocarbon chain that comprises a fully saturated (no double or triple bonds) hydrocarbon group. The alkyl group may have 1 to 25 carbon atoms (whenever it appears herein, a numerical range such as "1 to 25" refers to each integer in the given range; e.g., "1 to 25 carbon atoms" means that the alkyl group may consist of 1 carbon atom, 2 carbon atoms, 3 carbon atoms, etc., up to and including 25 carbon atoms, although the present definition also covers the occurrence of the term "alkyl" where no numerical range is designated). The alkyl group may also be a medium size alkyl having 1 to 18 carbon atoms. The alkyl group could also be a lower alkyl having 1 to 6 carbon atoms. The alkyl group of the compounds may be designated as "C$_4$" or "C$_1$-C$_4$ alkyl" or similar designations. By way of example only, "C$_1$-C$_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The alkenyl group may have 2 to 25 carbon atoms (whenever it appears herein, a numerical range such as "2 to 25" refers to each integer in the given range; e.g., "2 to 25 carbon atoms" means that the alkenyl group may consist of 2 carbon atom, 3 carbon atoms, 4 carbon atoms, etc., up to and including 25 carbon atoms, although the present definition also covers the occurrence of the term "alkenyl" where no numerical range is designated). The alkenyl group may also be a medium size alkenyl having 2 to 15 carbon atoms. The alkenyl group could also be a lower alkenyl having 1 to 6 carbon atoms. The alkenyl group of the compounds may be designated as "C$_4$" or "C$_2$-C$_4$ alkyl" or similar designations. An alkenyl group may be unsubstituted or substituted.

As used herein, "alkynyl" refers to an alkyl group that contains in the straight or branched hydrocarbon chain one or more triple bonds. The alkynyl group may have 2 to 25 carbon atoms (whenever it appears herein, a numerical range such as "2 to 25" refers to each integer in the given range; e.g., "2 to 25 carbon atoms" means that the alkynyl group may consist of 2 carbon atom, 3 carbon atoms, 4 carbon atoms, etc., up to and including 25 carbon atoms, although the present definition also covers the occurrence of the term "alkynyl" where no numerical range is designated). The alkynyl group may also be a medium size alkynyl having 2 to 15 carbon atoms. The alkynyl group could also be a lower alkynyl having 2 to 6 carbon atoms. The alkynyl group of the compounds may be designated as "C$_4$" or "C$_2$-C$_4$ alkyl" or similar designations. An alkynyl group may be unsubstituted or substituted.

As used herein, "aryl" or "aromatic" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a C$_6$-C$_{14}$ aryl group, a C$_6$-C$_{10}$ aryl group, or a C$_6$ aryl group (although the definition of C$_6$-C$_{10}$ aryl covers the occurrence of "aryl" when no numerical range is designated). Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms, that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or unsubstituted.

As used herein, "aralkyl" and "aryl(alkyl)" refer to an aryl group connected, as a substituent, via a lower alkylene group. The aralkyl group may have 6 to 20 carbon atoms (whenever it appears herein, a numerical range such as "6 to 20" refers to each integer in the given range; e.g., "6 to 20 carbon atoms" means that the aralkyl group may consist of 6 carbon atom, 7 carbon atoms, 8 carbon atoms, etc., up to and including 20 carbon atoms, although the present definition also covers the occurrence of the term "aralkyl" where no numerical range is designated). The lower alkylene and aryl group of an aralkyl may be substituted or unsubstituted. Examples include but are not limited to benzyl, 2-phenylalkyl, 3-phenylalkyl, and naphthylalkyl.

An "O-carboxy" group refers to a "RC(=O)O—" group in which R can be hydrogen, alkyl, alkenyl, alkynyl, cycloalkyl, cycloalkenyl, aryl, heteroaryl, heteroalicyclyl, aralkyl, (heteroaryl)alkyl or (heteroalicyclyl)alkyl, as defined herein. An O-carboxy may be substituted or unsubstituted.

A "thiocarbonyl" group refers to a "—C(=S)R" group in which R can be the same as defined with respect to O-carboxy. A thiocarbonyl may be substituted or unsubstituted.

A "trihalomethanesulfonamido" group refers to an "$X_3CS(O)_2N(R_A)$—" group wherein each X is a halogen, and $R_A$ hydrogen, alkyl, alkenyl, alkynyl, cycloalkyl, cycloalkenyl, cycloalkynyl, aryl, heteroaryl, heteroalicyclyl, aralkyl, (heteroaryl)alkyl or (heteroalicyclyl)alkyl.

The term "azido" as used herein refers to a —$N_3$ group.

A "mercapto" group refers to an "—SH" group.

A "carbonyl" group refers to a C=O group. Unless otherwise indicated, the carbonyl group may be substituted to form any of a ketone, amide, aldehyde, urea, and carbamate.

"Lower alkylene groups" refer to a $C_1$-$C_{25}$ straight-chained alkyl tethering groups, such as —$CH_2$-tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted." As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be unsubstituted or substituted.

As used herein, "alkoxy" or "alkyloxy" refers to the formula —OR wherein R is an alkyl, an alkenyl, an alkynyl, a cycloalkyl, a cycloalkenyl or a cycloalkynyl as defined above. A non-limiting list of alkoxys are methoxy, ethoxy, n-propoxy, 1-methylethoxy(isopropoxy), n-butoxy, iso-butoxy, sec-butoxy and tert-butoxy. An alkoxy may be substituted or unsubstituted.

As used herein, "acyl" refers to a hydrogen, alkyl, alkenyl, alkynyl, aryl, or heteroaryl connected, as substituents, via a carbonyl group. Examples include formyl, acetyl, propanoyl, benzoyl, and acryl. An acyl may be substituted or unsubstituted.

As used herein, "alkoxyalkyl" or "alkyloxyalkyl" refers to an alkoxy group connected, as a substituent, via a lower alkylene group. Examples include alkyl-O-alkyl- and alkoxy-alkyl- with the terms alkyl and alkoxy defined herein.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

As used herein, "aminoalkyl" refers to an amino group connected, as a substituent, via an alkylene group. Examples include $H_2N$-alkyl- with the term alkyl defined herein.

As used herein, "alkylcarboxyalkyl" refers to an alkyl group connected, as a substituent, to a carboxy group that is connected, as a substituent, to an alkyl group. Examples include alkyl-C(=O)O-alkyl- and alkyl-O—C(=O)-alkyl- with the term alkyl as defined herein.

As used herein, "alkylaminoalkyl" refers to an alkyl group connected, as a substituent, to an amino group that is connected, as a substituent, to an alkyl group. Examples include alkyl-NH-alkyl-, with the term alkyl as defined herein.

As used herein, "dialkylaminoalkyl" or "di(alkyl)aminoalkyl" refers to two alkyl groups connected, each as a substituent, to an amino group that is connected, as a substituent, to an alkyl group. Examples include

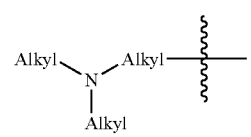

with the term alkyl as defined herein.

As used herein, "alkylaminoalkylamino" refers to an alkyl group connected, as a substituent, to an amino group that is connected, as a substituent, to an alkyl group that is connected, as a substituent, to an amino group. Examples include alkyl-NH-alkyl-NH—, with the term alkyl as defined herein.

As used herein, "alkylaminoalkylaminoalkylamino" refers to an alkyl group connected, as a substituent, to an amino group that is connected, as a substituent, to an alkyl group that is connected, as a substituent, to an amino group that is connected, as a substituent, to an alkyl group. Examples include alkyl-NH-alkyl-NH-alkyl-, with the term alkyl as defined herein.

As used herein, "arylaminoalkyl" refers to an aryl group connected, as a substituent, to an amino group that is connected, as a substituent, to an alkyl group. Examples include aryl-NH-alkyl-, with the terms aryl and alkyl as defined herein.

As used herein, "aminoalkyloxy" refers to an amino group connected, as a substituent, to an alkyloxy group. Examples include $H_2N$-alkyl-O— and $H_2N$-alkoxy- with the terms alkyl and alkoxy as defined herein.

As used herein, "aminoalkyloxyalkyl" refers to an amino group connected, as a substituent, to an alkyloxy group connected, as a substituent, to an alkyl group. Examples include $H_2N$-alkyl-O-alkyl- and $H_2N$-alkoxy-alkyl- with the terms alkyl and alkoxy as defined herein.

As used herein, "aminoalkylcarboxy" refers to an amino group connected, as a substituent, to an alkyl group connected, as a substituent, to a carboxy group. Examples include $H_2N$-alkyl-C(=O)O— and $H_2N$-alkyl-O—C(=O)— with the term alkyl as defined herein.

As used herein, "aminoalkylamino" refers to an amino group connected, as a substituent, to an alkyl group connected, as a substituent, to an amino group. Examples include $H_2N$-alkyl-NH— with the term alkyl as defined herein.

As used herein, "aminoalkylcarboxamido" refers to an amino group connected, as a substituent, to an alkyl group connected, as a substituent, to a carbonyl group connected, as a substituent to an amino group. Examples include $H_2N$-alkyl-C(=O)—NH— with the term alkyl as defined herein.

As used herein, "guanidinoalkyloxy" refers to a guanidinyl group connected, as a substituent, to an alkyloxy group. Examples include

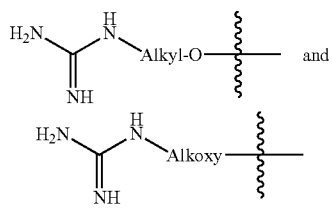

with the terms alkyl and alkoxy as defined herein.

As used herein, "guanidinoalkylcarboxy" refers to a guanidinyl group connected, as a substituent, to an alkyl group connected, as a substituent, to a carboxy group. Examples include

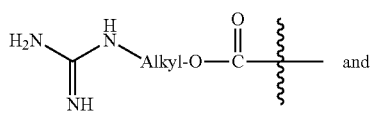

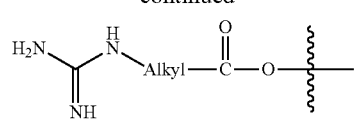

with the term alkyl as defined herein.

As used herein, "quaternaryammoniumalkylcarboxy" refers to a quaternized amino group connected, as a substituent, to an alkyl group connected, as a substituent, to a carboxy group. Examples include

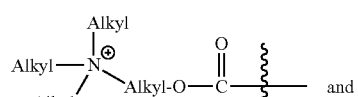

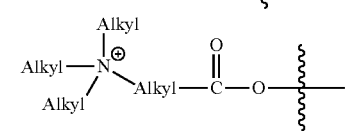

with the term alkyl as defined herein.

The term "halogen atom" or "halogen" as used herein, means any one of the radio-stable atoms of column 7 of the Periodic Table of the Elements, such as, fluorine, chlorine, bromine and iodine.

Where the numbers of substituents is not specified (e.g. haloalkyl), there may be one or more substituents present. For example "haloalkyl" may include one or more of the same or different halogens.

As used herein, the term "amino acid" refers to any amino acid (both standard and non-standard amino acids), including, but not limited to, α-amino acids, β-amino acids, γ-amino acids and δ-amino acids. Examples of suitable amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Additional examples of suitable amino acids include, but are not limited to, ornithine, hypusine, 2-aminoisobutyric acid, dehydroalanine, gamma-aminobutyric acid, citrulline, beta-alanine, alpha-ethyl-glycine, alpha-propyl-glycine and norleucine.

A linking group is a divalent moiety used to link one steroid to another steroid. In some embodiments, the linking group is used to link a first CSA compound with a second CSA compound (which may be the same or different). An example of a linking group is $(C_1-C_{10})$ alkyloxy-$(C_1-C_{10})$ alkyl.

Commonly understand nomenclature and molecule representations are described and utilized throughout the specification. For example, a skilled artisan would readily appreciate that the following two structural representations are equivalent (wherein A, B, C, and D are unspecified functional groups):

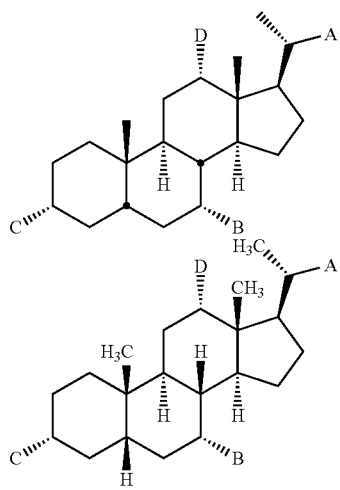

The terms "P.G." or "PG" or "protecting group" or "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls and alkoxycarbonyls (e.g., t-butoxycarbonyl (Boc), acetyl, or isobutyryl); arylalkylcarbonyls and arylalkoxycarbonyls (e.g., benzyloxycarbonyl or CBz, fluorenylmethylcarbonyl or Fmoc); substituted methyl ether (e.g. methoxymethyl ether or MOM); substituted ethyl ether; a substituted benzyl ether; tetrahydropyranyl ether; silyls (e.g., trimethylsilyl, triethylsilyl, triisopropylsilyl, t-butyldimethylsilyl, triisopropylsilyloxy-methyl, [2-(trimethylsilyl)ethoxy]methyl or t-butyldiphenylsilyl); esters (e.g. benzoate ester); carbonates (e.g. methoxymethylcarbonate); sulfonates (e.g. tosylate or mesylate); acyclic ketal (e.g. dimethyl acetal); cyclic ketals (e.g., 1,3-dioxane, 1,3-dioxolanes, and those described herein); acyclic acetal; cyclic acetal (e.g., those described herein); acyclic hemiacetal; cyclic hemiacetal; cyclic dithioketals (e.g., 1,3-dithiane or 1,3-dithiolane); orthoesters (e.g., those described herein) and triarylmethyl groups (e.g., trityl; monomethoxytrityl (MMTr); 4,4'-dimethoxytrityl (DMTr); 4,4',4''-trimethoxytrityl (TMTr); and those described herein). Amino-protecting groups are known to those skilled in the art, and carbamates such as Fmoc, Boc, and CBz, as well as allyl, and acyl are particularly preferred protecting groups. In general, the species of protecting group is not critical unless explicitly defined, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the disclosure.

Methods of Treatment, Uses, and Medicaments

Infection is a major complication that can affect orthopedic operations and can have a devastating effect on morbidity. In particular, bone infections can be challenging to treat once they are established. Disclosed herein are methods of treating or preventing an infection in a subject in need thereof by the administration of one or more or cationic steroidal antimicrobial (CSA) compounds (or ceragenins), or pharmaceutically acceptable salts thereof. Disclosed herein are also CSA compositions comprising at least one CSA compound, or pharmaceutically acceptable sat thereof, for use in the treatment prevention of infections in subjects having a bone disease, a bone implant, or a broken bone. Some embodiments include methods of treating or preventing infection while concurrently promoting osteogenesis in a subject. Some embodiments include methods of treating or preventing infection while concurrently treating or preventing a bone disease, a broken bone, a bone infection, or a bone implant with the administration of one or more CSA compounds, or pharmaceutically acceptable salts thereof.

In some embodiments, the CSA compositions or methods further comprise administering at least one growth factor. The growth factor administered may be a bone growth factor, which may enhance osteogenesis in the subject. In some embodiments, the bone growth factor is recombinant bone morphogenetic protein. In some embodiments, the recombinant bone morphogenetic protein is recombinant human bone morphogenetic protein. In some embodiments, the bone morphogenetic protein is BMP-2. In other embodiments the bone morphogenetic protein is BMP-2, BMP-3, BMP-4, BMP-5, BMP-6, BMP-7, and/or a combination of any of the aforementioned BMPs. In some embodiments, the bone growth factor is INFUSE® BMP-2 and/or OP-1 BMP-7. The interaction between the bone growth factor and CSA compound may be a synergistic interaction resulting in osteogenesis at levels higher than expected from individual treatment using only a CSA compound or only a growth factor. In some exemplary embodiments, the method further comprises administering an osteogenic nutrient, osteogenic supplement, or combinations thereof.

In some embodiments, one or more CSA compounds are administered to a subject having a broken bone. Examples of broken bones include fractures (including traumatic fractures, stress fractures, and fractures characterized by partial breakages such as greenstick fractures); critical sized bone defects; distraction osteogenesis; surgical bone alterations (including spine fusion surgery); and bone disruption resulting from a joint replacement, an orthopaedic implant (bone implant), or a biopsy. In some embodiments, subject may have a non-healing bone conditions, such as fractures or surgical removal or grafting of bones.

The compositions disclosed herein can be administered to any bone, anywhere it is desirable to promote bone healing or bone synthesis; e.g., the compositions can be administered to fracture fixation (such as fracture healing) in broken bones, or treatment of osteoporotic bone (i.e., to promote osteogenesis and strengthen the bone). The compositions are also useful to strengthen or repair osteoporotic bone, where there is not a lot of nascent bone material to start with. In this exemplary embodiment, the compositions may promote accelerated osteogenesis within the osteoporotic bone, thereby strengthening the bone. This can be accomplished with little or no destruction of the osteoporotic bone; e.g., the compositions may be simply coated onto the osteoporotic bone, or alternatively, used to fill in defects. In addition, the compositions can be used to reconstruct a segmental defect in the case of missing bone, e.g., following tumor resection, polytrauma, or combinations thereof. In general, the compositions can be administered anywhere it is desired to promote osteogenesis within or adjacent to bone as well as treat, prevent, or combat infection, particularly lowering the risk of developing a bone infection. Consequently, the CSA compositions disclosed herein are well-suited for combination therapy (ameliorating infection and promoting osteogenesis) as well as promoting individual mono-therapies.

In some embodiments, one or more CSA compounds are administered with additional compounds that provide therapeutic effects towards bone diseases or broken bones. In some embodiments, the CSA compound is administered with one or more bisphosphonates. Examples of bisphosphonates include Etidronate, Elodronate, Tiladronate, Pamidronate, Neridronate, Olpadronate, Alendronate, Ibandronate, Residronate, and/or Zoledronate. In some embodiments, the CSA compound is administered with calcium and/or vitamin D. In some embodiments, the CSA compound is administered with compounds for the treatment of osteoporosis. In some embodiments, the CSA compound is administered with Teriparatide, strontium ranelate, raloxifene, and/or Denosumab. In some embodiments, the administration of a single CSA compound, or pharmaceutically acceptable salt thereof, provides efficacy for treating or preventing infections as well as efficacy for treating or preventing a bone disease, a broken bone, a bone infection, or a bone implant. In some embodiments, the administration of two or more CSA compounds, or pharmaceutically acceptable salt thereof, provides efficacy for treating or preventing infections as well as efficacy for treating or preventing a bone disease, a broken bone, a bone infection, or a bone implant. Such administration may also promote healing and/or osteogenesis. When multiple CSA compounds are administered, one or all administered compounds may have anti-infective properties as well as therapeutically desirable properties for treating or preventing a bone disease, a broken bone, a bone infection, or a bone implant.

In some embodiments, the subject is a mammal. Examples of mammals include horses, cattle, pigs, and humans. In some embodiments, the subject is a human. In some embodiments, the subject is in need of osteogenesis and the compound of Formula (I) promotes osteogenesis. In some embodiments, the subject has a bone disease, a broken bone, a bone infection, or a bone implant. In some embodiments, the subject has a bone disease selected from the group consisting of bone resorption, osteoarthritis, osteoporosis, osteomalacia, osteitis fibrosa cystica, osteochondritis dissecans, osteomalacia, osteomyelitis, osteopenia, osteonecrosis, and porotic hyperostosis. In some embodiments, the subject has a broken bone and the broken bone results from a traumatic fracture; a critical sized bone defect; distraction osteogenesis; spine fusion surgery; joint replacement; an orthopaedic implant; or a biopsy. Orthopaedic implants are well known in the art and replace a missing joint or bone or support a damaged bone. Common types of implants include pins, rods, screws and plates.

In some embodiments, the infection is a bacterial infection. In some embodiments, the infection is a drug-resistant bacterial infection. In some embodiments, the infection is MRSA or TRPA. In some embodiments, the infection is a *staphylococcus* or *pseudomonas* bacterial infection. In some embodiments, the infection is a gram negative bacterial infection. In some embodiments, the infection is a bone infection. In some embodiments, the infection is an *S. aureus* or *P. aeruginosa* infection.

Some embodiments are directed to methods of treating or preventing an infection in a subject in need thereof, comprising administering to the subject a compound of Formula (I), or pharmaceutically acceptable salt thereof:

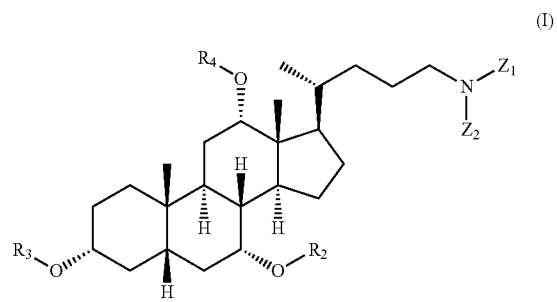

(I)

wherein, $Z_1$ and $Z_2$ are independently selected from the group consisting of optionally substituted alkyl; optionally substituted alkenyl; and optionally substituted alkynyl;

$R_2$, $R_3$, and $R_4$, are independently selected from the group consisting of optionally substituted protected or unprotected amino-$C_a$-alkyl; optionally substituted protected or unprotected amino-$C_a$-alkylcarbonyl; and optionally substituted protected or unprotected amino-$C_a$-alkylthiocarbonyl; and a is 2-5.

In some embodiments, $Z_1$ and $Z_2$ are optionally substituted alkyl. In some embodiments, $Z_1$ and $Z_2$ are unsubstituted alkyl. In some embodiments, $Z_1$ and $Z_2$ are optionally substituted alkenyl. In some embodiments, $Z_1$ and $Z_2$ are unsubstituted alkenyl. In some embodiments, $Z_1$ and $Z_2$ are optionally substituted alkynyl. In some embodiments, $Z_1$ and $Z_2$ are unsubstituted alkynyl.

In some embodiments, $Z_1$ and $Z_2$ are independently selected from the group consisting of $C_1$-$C_{20}$-alkyl; $C_3$-$C_{20}$-alkenyl; and $C_3$-$C_{20}$-alkynyl. In some embodiments, $Z_1$ and $Z_2$ are independently selected from the group consisting of $C_3$-$C_{10}$-alkyl; $C_3$-$C_{10}$-alkenyl; and $C_3$-$C_{10}$-alkynyl. In some embodiments, $Z_1$ and $Z_2$ are independently selected from the group consisting of $C_5$-$C_8$-alkyl; $C_5$-$C_8$-alkenyl; and $C_5$-$C_8$-alkynyl. In some embodiments, $Z_1$ and $Z_2$ are $C_5$-$C_8$-alkyl. In some embodiments, $Z_1$ and $Z_2$ are unsubstituted $C_5$-$C_8$-alkyl.

In some embodiments, $R_2$, $R_3$, and $R_4$, are amino-$C_a$-alkyl or amino-$C_a$-alkylcarbonyl. In some embodiments, $R_2$, $R_3$, and $R_4$, are amino-$C_a$-alkyl. In some embodiments, $R_2$, $R_3$, and $R_4$, are amino-$C_a$-alkylcarbonyl. In some embodiments, a is 2. In some embodiments, a is 3. In some embodiments, a is 4. In some embodiments, a is 5.

In some embodiments, the protected amino-$C_a$-alkyl and the protected amino-$C_a$-alkylcarbonyl are protected with a group independently selected from Fmoc, Boc, allyl, acetyl, benzyl, or CBz. In some embodiments, $R_2$, $R_3$, and $R_4$, are independently selected from the group consisting of carbamate protected or unprotected amino-$C_a$-alkyl and carbamate protected or unprotected amino-$C_a$-alkylcarbonyl. In some embodiments, $R_2$, $R_3$, and $R_4$, are independently selected from the group consisting of Fmoc protected or unprotected amino-$C_a$-alkyl and Fmoc protected or unprotected amino-$C_a$-alkylcarbonyl. In some embodiments, $R_2$, $R_3$, and $R_4$, are independently selected from the group consisting of Boc protected or unprotected amino-$C_a$-alkyl and Boc protected or unprotected amino-$C_a$-alkylcarbonyl.

In some embodiments, the compound of Formula (I) is:

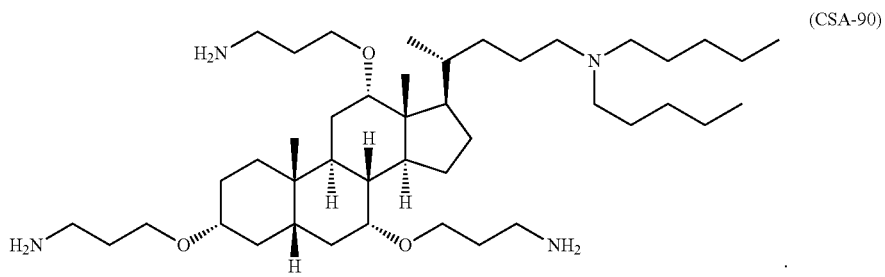
(CSA-90)

In some embodiments, the compound of Formula (I) is:

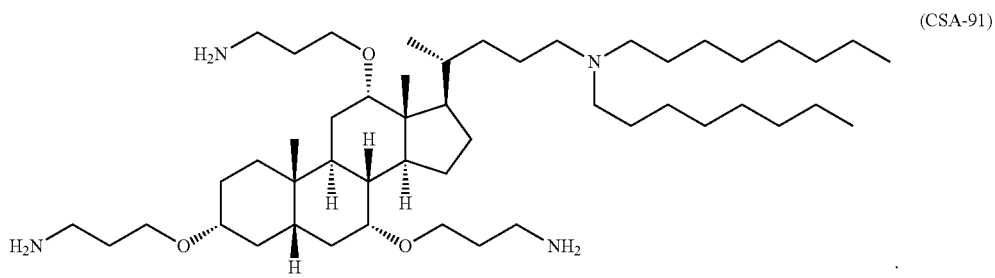
(CSA-91)

In some embodiments, the compound of Formula (I) is:

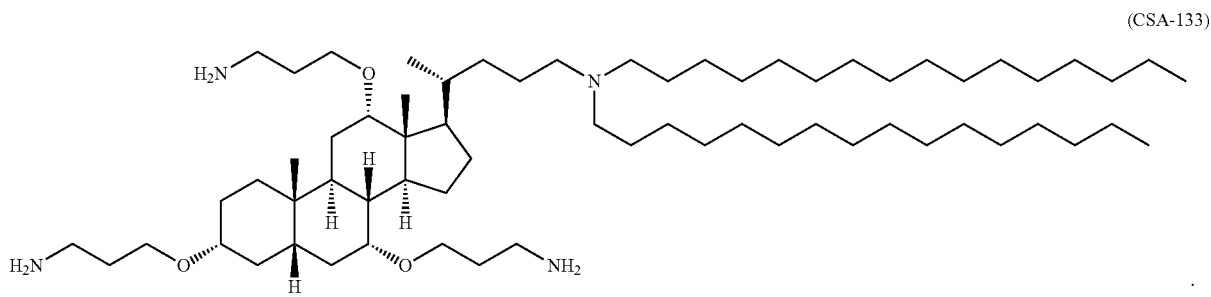
(CSA-133)

In some embodiments, the optional substituent is fluorine. In some embodiments, the compound is not optionally substituted.

In some embodiments, the compound of Formula (I) is selected from the group consisting of:

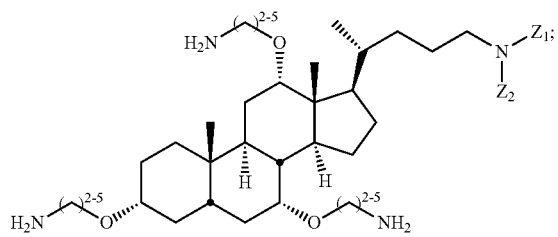

-continued

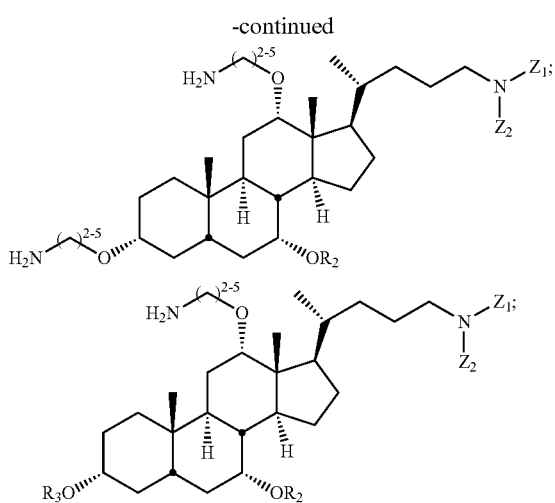

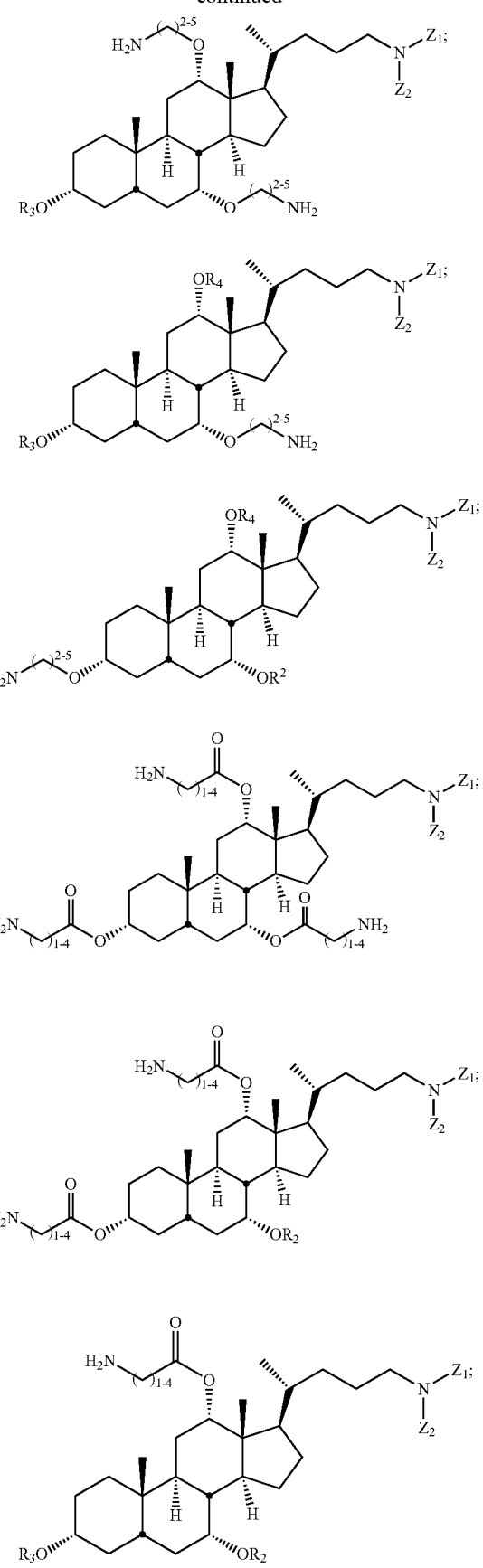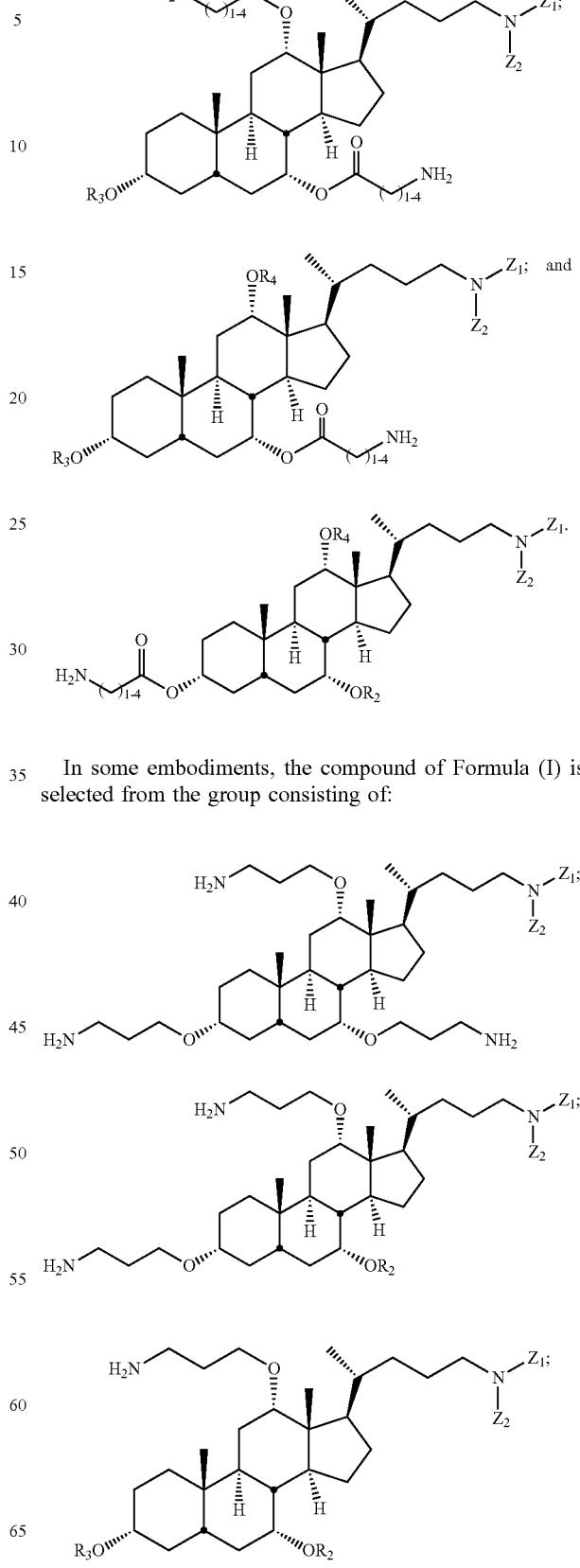
In some embodiments, the compound of Formula (I) is selected from the group consisting of:
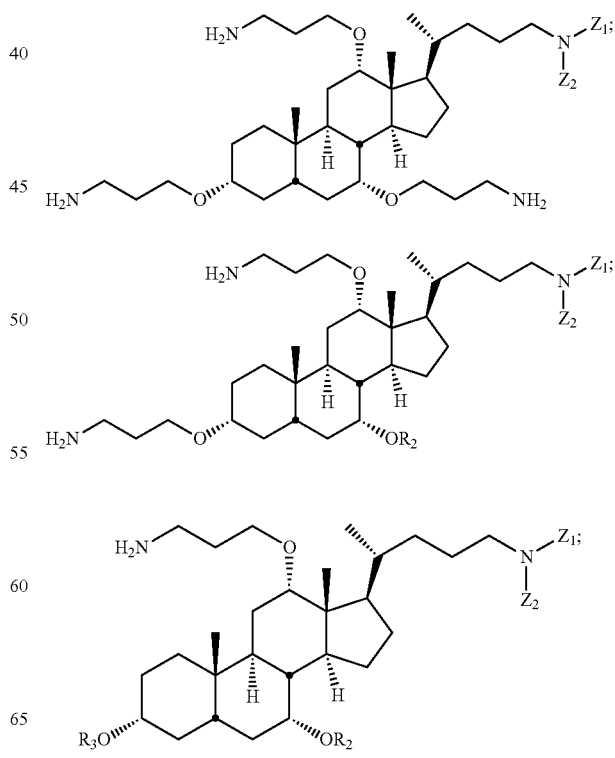

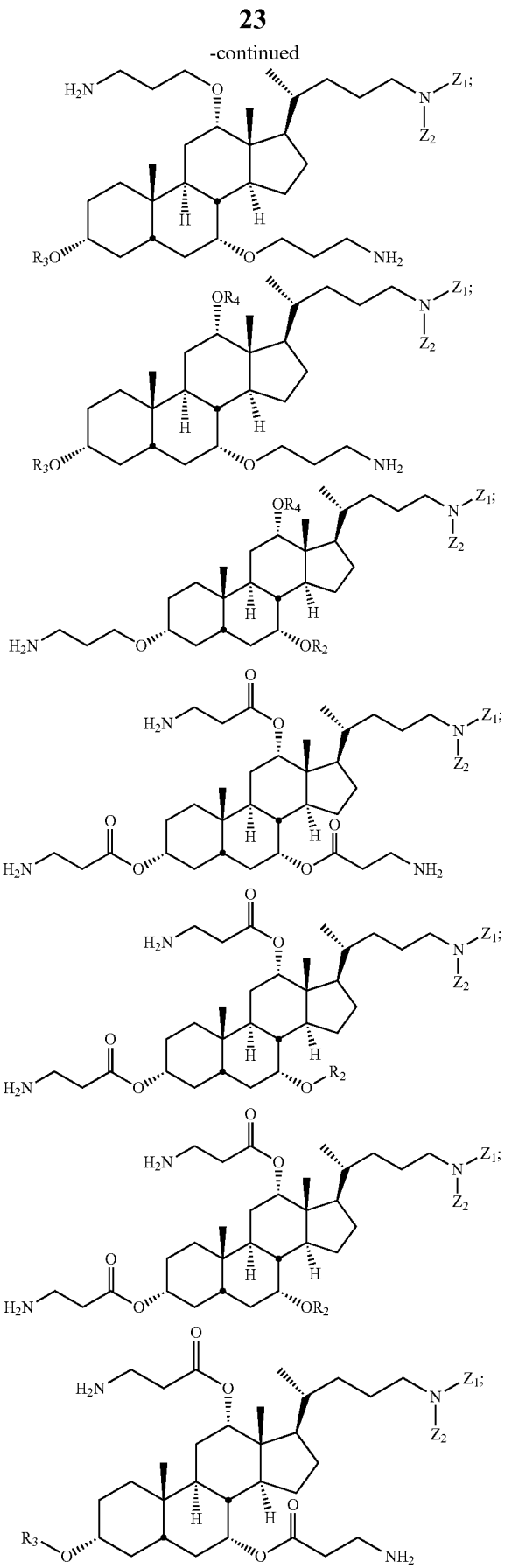
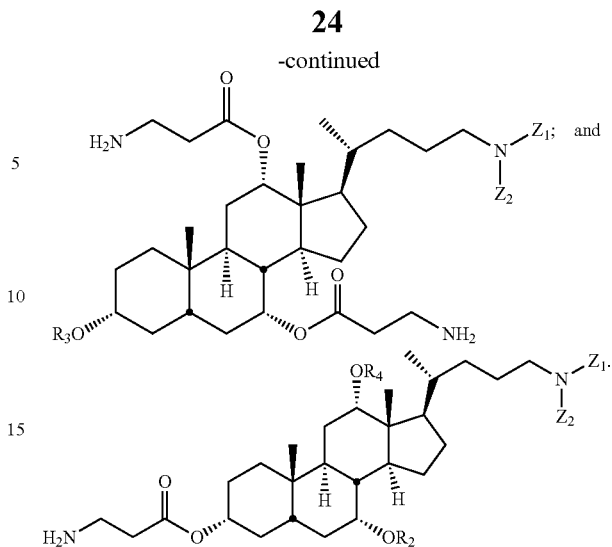

Some embodiments comprise a compound of Formula (I), or pharmaceutically acceptable salt thereof, and a pharmaceutically acceptable excipient. Pharmaceutically acceptable salts and excipients are described in more detail below.

Pharmaceutically Acceptable Salts

The compounds and compositions disclosed herein are optionally prepared as pharmaceutically acceptable salts. The term "pharmaceutically acceptable salt" as used herein is a broad term, and is to be given its ordinary and customary meaning to a skilled artisan (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluenesulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the pharmaceutically acceptable salt is a hydrochloride salt. In some embodiments, the pharmaceutically acceptable salt is a mono-hydrochloride salt, a di-hydrochloride salt, a tri-hydrochloride salt, or a tetra-hydrochloride salt. Some embodiments are directed to a sulfuric acid addition salt or sulfonic acid addition salt of a CSA compound. In some embodiments, the sulfonic acid addition salt is a disulfonic acid addition salt. In some embodiments, the sulfonic acid addition salt is a 1,5-naphthalenedisulfonic acid addition salt. In some embodiments, the acid addition salt is a mono-addition salt. In other embodiments, the acid addition salt is a di-addition salt. In other embodiments, the acid addition salt is a tetra-addition salt.

In some embodiments, the pharmaceutically acceptable salt is a benzoic acid salt. In other embodiments, the acid addition salt is a benzenesulphonic acid salt. In other embodiments, the acid addition salt is a citric acid salt. In other embodiments, the acid addition salt is a fumaric acid salt. In other embodiments, the acid addition salt is a galactaric acid (mucic acid) salt. In other embodiments, the acid addition salt is a1-hydroxy-2-naphthoic acid salt. In other embodiments, the acid addition salt is a pamoic acid salt. In other embodiments, the acid addition salt is a phosphoric acid salt. In other embodiments, the acid addition salt is a succinic acid salt. In other embodiments, the acid addition salt is a L-tartaric acid salt.

Pharmaceutical Compositions

While it is possible for the compounds described herein to be administered alone, it may be preferable to formulate the compounds as pharmaceutical compositions (e.g., formulations). As such, in yet another aspect, pharmaceutical compositions useful in the methods and uses of the disclosed embodiments are provided. A pharmaceutical composition is any composition that may be administered in vitro or in vivo or both to a subject in order to treat or ameliorate a condition. In a preferred embodiment, a pharmaceutical composition may be administered in vivo. A subject may include one or more cells or tissues, or organisms. In some exemplary embodiments, the subject is an animal. In some embodiments, the animal is a mammal. The mammal may be a human or primate in some embodiments. A mammal includes any mammal, such as by way of non-limiting example, cattle, pigs, sheep, goats, horses, camels, buffalo, cats, dogs, rats, mice, and humans.

As used herein the terms "pharmaceutically acceptable" and "physiologically acceptable" mean a biologically compatible formulation, gaseous, liquid or solid, or mixture thereof, which is suitable for one or more routes of administration, in vivo delivery, or contact. A formulation is compatible in that it does not destroy activity of an active ingredient therein (e.g., a CSA compound or ceragenin), or induce adverse side effects that far outweigh any prophylactic or therapeutic effect or benefit.

In an embodiment, the pharmaceutical compositions may be formulated with pharmaceutically acceptable excipients such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, it may be preferred that the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents).

Formulations, e.g., for parenteral or oral administration, are most typically solids, liquid solutions, emulsions or suspensions, while inhalable formulations for pulmonary administration are generally liquids or powders, with powder formulations being generally preferred. A preferred pharmaceutical composition may also be formulated as a lyophilized solid that is reconstituted with a physiologically compatible solvent prior to administration. Alternative pharmaceutical compositions may be formulated as syrups, creams, ointments, tablets, and the like.

Compositions may contain one or more excipients. Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g., dextran sulfate); glycoaminoglycans and glycosaminoglycan-like compounds (e.g., hyaluronic acid); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids such as oleic acid may be used in the preparation of injectables.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, and complexation.

Many therapeutics have undesirably short half-lives and/or undesirable toxicity. Thus, the concept of improving half-life or toxicity is applicable to various treatments and fields. Pharmaceutical compositions can be prepared, however, by complexing the therapeutic with a biochemical moiety to improve such undesirable properties. Proteins are a particular biochemical moiety that may be complexed with a CSA compound for administration in a wide variety of applications. In some embodiments, one or more CSAs are complexed with a protein. In some embodiments, one or more CSA compounds are complexed with a protein to increase the CSA compound's half-life. In other embodiments, one or more CSA compounds are complexed with a protein to decrease the CSA compound's toxicity. Albumin is a particularly preferred protein for complexation with a CSA compound. In some embodiments, the albumin is fat-free albumin.

With respect to the CSA therapeutic, the biochemical moiety for complexation can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the weight ratio of albumin to CSA compound is about 18:1 or less, such as about 9:1 or less. In some embodiments, the CSA compound is coated with albumin.

Alternatively, or in addition, non-biochemical compounds can be added to the pharmaceutical compositions to reduce the toxicity of the therapeutic and/or improve the half-life. Suitable amounts and ratios of an additive that can reduce toxicity can be determined via a cellular assay. With respect to the CSA therapeutic, toxicity reducing compounds can be added to the pharmaceutical composition as 0.25, 0.5, 0.75, 1, 1.5, 2, 2.5, 3, 3.5, 4, 4.5, 5, 10, 20, 50, or 100 weight equivalents, or a range bounded by any two of the aforementioned numbers, or about any of the numbers. In some embodiments, the toxicity reducing compound is a cocoamphodiacetate such as Miranol® (disodium cocoamphodiacetate). In other embodiments, the toxicity reducing compound is an amphoteric surfactant. In some embodiments, the toxicity reducing compound is a surfactant. In other embodiments, the molar ratio of cocoamphodiacetate to CSA compound is between about 8:1 and 1:1, preferably about 4:1. In some embodiments, the toxicity reducing compound is allantoin.

In some embodiments, a CSA composition is prepared utilizing one or more sufactants. In specific embodiments, the CSA compound is complexed with one or more poloxamer surfactants. Poloxamer surfactants are nonionic triblock copolymers composed of a central hydrophobic chain of polyoxypropylene (poly(propylene oxide)) flanked by two hydrophilic chains of polyoxyethylene (poly(ethylene oxide)). In some embodiments, the poloxamer is a liquid, paste, or flake (solid). Examples of suitable poloxamers include those by the trade names Synperonics, Pluronics, or Kolliphor. In some embodiments, one or more of the poloxamer surfactant in the composition is a flake poloxamer. In some embodiments, the one or more poloxamer surfactant in the composition has a molecular weight of about 3600 g/mol for the central hydrophobic chain of polyoxypropylene and has about 70% polyoxyethylene content. In some embodiments, the ratio of the one or more poloxamer to CSA compound is between about 50:1; about 40:1; about 30:1; about 20:1; about 10:1; about 5:1; about 1:1; about 1:10; about 1:20; about 1:30; about 1:40; or about 1:50. In other embodiments, the ratio of the one or more poloxamer to CSA compound is between 50:1; 40:1; 30:1; 20:1; 10:1; 5:1; 1:1; 1:10; 1:20; 1:30; 1:40; or 1:50. In some embodiments, the ratio of the one or more poloxamer to CSA compound is between about 50:1 to about 1:50. In other embodiments, the ratio of the one or more poloxamer to CSA compound is between about 30:1 to about 3:1. In some embodiments, the poloxamer is Pluronic F127.

The amount of poloxamer may be based upon a weight percentage of the composition. In some embodiments, the amount of poloxamer is about 10%, 15%, 20%, 25%, 30%, 35%, 40%, about any of the aforementioned numbers, or a range bounded by any two of the aforementioned numbers or the formulation. In some embodiments, the one or more poloxamer is between about 10% to about 40% by weight of a formulation administered to the patient. In some embodiments, the one or more poloxamer is between about 20% to about 30% by weight of the formulation. In some embodiments, the formulation contains less than about 50%, 40%, 30%, 20%, 10%, 5%, or 1% of CSA, or about any of the aforementioned numbers. In some embodiments, the formulation contains less than about 20% by weight of CSA compound.

The above described poloxamer formulations are particularly suited for the methods of treatment, device coatings, preparation of unit dosage forms (e.g., solutions, mouthwashes, injectables), etc.

In one embodiment, the compounds described herein may be formulated for oral administration in a lipid-based formulation suitable for low solubility compounds. Lipid-based formulations can generally enhance the oral bioavailability of such compounds.

As such, a pharmaceutical composition comprIn some embodiments a therapeutically or prophylactically effective amount of a compound described herein, together with at least one pharmaceutically acceptable excipient selected from the group consisting of-medium chain fatty acids or propylene glycol esters thereof (e.g., propylene glycol esters of edible fatty acids such as caprylic and capric fatty acids) and pharmaceutically acceptable surfactants such as polyoxyl 40 hydrogenated castor oil.

In an alternative preferred embodiment, cyclodextrins may be added as aqueous solubility enhancers. Preferred cyclodextrins include hydroxypropyl, hydroxyethyl, glucosyl, maltosyl and maltotriosyl derivatives of α-, β-, and γ-cyclodextrin. A particularly preferred cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprIn some embodimentss about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the embodiments in the composition.

In some exemplary embodiments, a CSA compound comprises a multimer (e.g., a dimer, trimer, tetramer, or higher order polymer). In some exemplary embodiments, the CSA compounds can be incorporated into pharmaceutical compositions or formulations. Such pharmaceutical compositions/formulations are useful for administration to a subject, in vivo or ex vivo. Pharmaceutical compositions and formulations include carriers or excipients for administration to a subject.

Such formulations include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

A pharmaceutical composition and/or formulation contains a total amount of the active ingredient(s) sufficient to achieve an intended therapeutic effect.

Dosages

The formulations may, for convenience, be prepared or provided as a unit dosage form. Preparation techniques include bringing into association the active ingredient (e.g., CSA/ceragenin) and a pharmaceutical carrier(s) or excipient(s). In general, formulations are prepared by uniformly and intimately associating the active ingredient with liquid carriers or finely divided solid carriers or both, and then, if necessary, shaping the product. For example, a tablet may be made by compression or molding. Compressed tablets may be prepared by compressing, in a suitable machine, an active ingredient (e.g., a CSA/ceragenin) in a free-flowing form such as a powder or granules, optionally mixed with a binder, lubricant, inert diluent, preservative, surface-active or dispersing agent. Molded tablets may be produced by molding, in a suitable apparatus, a mixture of powdered compound (e.g., CSA/ceragenin) moistened with an inert liquid diluent. The tablets may optionally be coated or scored and may be formulated so as to provide a slow or controlled release of the active ingredient therein.

Compounds (e.g., CSAs/ceragenins), including pharmaceutical formulations can be packaged in unit dosage forms for ease of administration and uniformity of dosage. A "unit dosage form" as used herein refers to a physically discrete unit suited as unitary dosages for the subject to be treated; each unit containing a predetermined quantity of compound optionally in association with a pharmaceutical carrier (excipient, diluent, vehicle or filling agent) which, when administered in one or more doses, is calculated to produce a desired effect (e.g., prophylactic or therapeutic effect or benefit). Unit dosage forms can contain a daily dose or unit, daily sub-dose, or an appropriate fraction thereof, of an administered compound (e.g., CSA/ceragenin). Unit dosage forms also include, for example, capsules, troches, cachets, lozenges, tablets, ampules and vials, which may include a composition in a freeze-dried or lyophilized state; a sterile liquid carrier, for example, can be added prior to administration or delivery in vivo. Unit dosage forms additionally include, for example, ampules and vials with liquid compositions disposed therein. Unit dosage forms further include compounds for transdermal administration, such as "patches" that contact with the epidermis of the subject for an extended or brief period of time. The individual unit dosage forms can be included in multi-dose kits or containers. Pharmaceutical formulations can be packaged in single or multiple unit dosage forms for ease of administration and uniformity of dosage.

Compounds (e.g., CSAs/ceragenins) can be administered in accordance with the methods at any frequency as a single bolus or multiple dose e.g., one, two, three, four, five, or more times hourly, daily, weekly, monthly, or annually or between about 1 to 10 days, weeks, months, or for as long as appropriate. Exemplary frequencies are typically from 1-7 times, 1-5 times, 1-3 times, 2-times or once, daily, weekly or monthly. Timing of contact, administration ex vivo or in vivo delivery can be dictated by the infection, pathogenesis, symptom, pathology or adverse side effect to be treated. For example, an amount can be administered to the subject substantially contemporaneously with, or within about 1-60 minutes or hours of the onset of a symptom or adverse side effect, pathogenesis, or vaccination. Long-acting pharmaceutical compositions may be administered twice a day, once a day, once every two days, three times a week, twice a week, every 3 to 4 days, or every week depending on half-life and clearance rate of the particular formulation. For example, in an embodiment, a pharmaceutical composition contains an amount of a compound as described herein that is selected for administration to a patient on a schedule selected from: twice a day, once a day, once every two days, three times a week, twice a week, and once a week.

Localized delivery is also contemplated, including but not limited to delivery techniques in which the compound is implanted, injected, infused, or otherwIn some embodiments locally delivered. Localized delivery is characterized by higher concentrations of drug at the site of desired action (e.g., the tumor or organ to be treated) versus systemic concentrations of the drug. Well-known localized delivery forms can be used, including long-acting injections; infusion directly into the site of action; depot delivery forms; controlled or sustained delivery compositions; transdermal patches; infusion pumps; and the like. The CSA compound can further be incorporated into a biodegradable or bioerodible material or be put into or on a medical device.

Doses may vary depending upon whether the treatment is therapeutic or prophylactic, the onset, progression, severity, frequency, duration, probability of or susceptibility of the symptom, the type pathogenesis to which treatment is directed, clinical endpoint desired, previous, simultaneous or subsequent treatments, general health, age, gender or race of the subject, bioavailability, potential adverse systemic, regional or local side effects, the presence of other disorders or din some embodimentsases in the subject, and other factors that will be appreciated by the skilled artisan (e.g., medical or familial history). Dose amount, frequency or duration may be increased or reduced, as indicated by the clinical outcome desired, status of the infection, symptom or pathology, any adverse side effects of the treatment or therapy. The skilled artisan will appreciate the factors that may influence the dosage, frequency and timing required to provide an amount sufficient or effective for providing a prophylactic or therapeutic effect or benefit. The exact dosage will be determined by the practitioner, in light of factors related to the subject that requires treatment. Dosage and administration are adjusted to provide sufficient levels of the active agent(s) or to maintain the desired effect. It will be appreciated that treatment as described herein includes preventing a disease, ameliorating symptoms, slowing disease progression, reversing damage, or curing a disease.

The dosage may range broadly, depending upon the desired effects and the therapeutic indication. Alternatively dosages may be based and calculated upon the surface area of the patient, as understood by those of skill in the art. Although the exact dosage will be determined on a drug-by-drug basis, in most cases, some generalizations regarding the dosage can be made. The systemic daily dosage regimen for an adult human patient may be, for example, an oral dose of between 0.01 mg and 3000 mg of the active ingredient, preferably between 1 mg and 700 mg, e.g. 5 to 200 mg. In some embodiments, the daily dosage regimen is 1 mg, 5 mg, 10, mg, 25 mg, 50 mg, 75 mg, 100 mg, 150 mg, 200 mg, 250 mg, 300 mg, 350 mg, 400 mg, 450 mg, 500 mg, 550 mg, 600 mg, 650 mg, 700 mg, or about any of the aforementioned numbers or a range bounded by any two of the aforementioned numbers. The dosage may be a single one or a series of two or more given in the course of one or more days, as is needed by the subject. In some embodiments, the compounds will be administered for a period of continuous therapy, for example for a week or more, or for months or years. Doses tailored for particular types of cancers or particular patients can be selected based, in part, on the $GI_{50}$, TGI, and $LC_{50}$ values set forth in the Examples that follow. Particularly preferred formulations for oral dosage include tablet or solutions, particularly solutions compatible with IV administration or solutions compatible with oral administration/use.

In instances where human dosages for compounds have been established for at least some condition, those same dosages may be used, or dosages that are between about 0.1% and 500%, more preferably between about 25% and 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or conditions.

Dosage amount and interval may be adjusted individually to provide plasma levels of the active moiety which are sufficient to maintain the modulating effects, or minimal effective concentration (MEC). For example, therapeutic dosages may result in plasma levels of 0.05 µg/mL, 0.1 µg/mL, 0.5 µg/mL, 1 µg/mL, 5 µg/mL, 10 µg/mL, 15 µg/mL, 20 µg/mL, 25 µg/mL, 30 µg/mL, 35 µg/mL, 40 µg/mL, 45 µg/mL, 50 µg/mL, 55 µg/mL, 60 µg/mL, 65 µg/mL, 70 µg/mL, 75 µg/mL, 80 µg/mL, 85 µg/mL, 90 µg/mL, 95 µg/mL, 100 µg/mL, a range bounded by any two of the aforementioned numbers, or about any of the aforementioned numbers and ranges. In some embodiments, the therapeutic dose is sufficient to establish plasma levels in the range of about 0.1 µg/mL to about 10 µg/mL. In other embodiments, the therapeutic dose is sufficient to establish plasma levels in the range of 1 μg/mL to 20 μg/mL. The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

As described herein, the methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, e.g., serially, whereas in simultaneous therapy, effective dosages of two or more active ingredients are administered together. Various sequences of intermittent combination therapy may also be used.

Co-Administration:

As used herein, "co-administration" means concurrently or administering one substance followed by beginning the administration of a second substance within 24 hours, 20 hours, 16 hours, 12 hours, 8 hours, 4 hours, 1 hour, 30 minutes, 15 minutes, 5 minutes, 1 minute, a range bounded by any two of the aforementioned numbers, and/or about any of the aforementioned numbers.

In some embodiments, one or more CSA/ceragenin are co-administered. In other embodiments, the co-administration of CSA/ceragenin accounts for their therapeutic benefit. In some embodiments, co-administration is concurrent.

Some embodiments are directed to the use of companion diagnostics to identify an appropriate treatment for the patient. A companion diagnostic is an in vitro diagnostic test or device that provides information that is essential for the safe and effective use of a corresponding therapeutic product. Such tests or devices can identify patients likely to be at risk for adverse reactions as a result of treatment with a particular therapeutic product. Such tests or devices can also monitor responsiveness to treatment (or estimate responsiveness to possible treatments). Such monitoring may include schedule, dose, discontinuation, or combinations of therapeutic agents. In some embodiments, the CSA/ceragenin is selected by measuring a biomarker in the patient. The term biomarker includes, but is not limited to, genetic regulation, protein levels, RNA levels, and cellular responses such as cytotoxicity.

Synthesis of CSA Compounds:

Compounds described herein can be prepared by known methods, especially known methods previously published by the inventors. A skilled artisan will readily understand that minor variations of starting materials and reagents may be utilized to prepare known and novel cationic steroidal antimicrobials. Schematically, for example, the preparation of certain compounds can be accomplished according to Schemes 1 and 2 as follows:

Scheme 1: Ether-Containing CSA Compounds

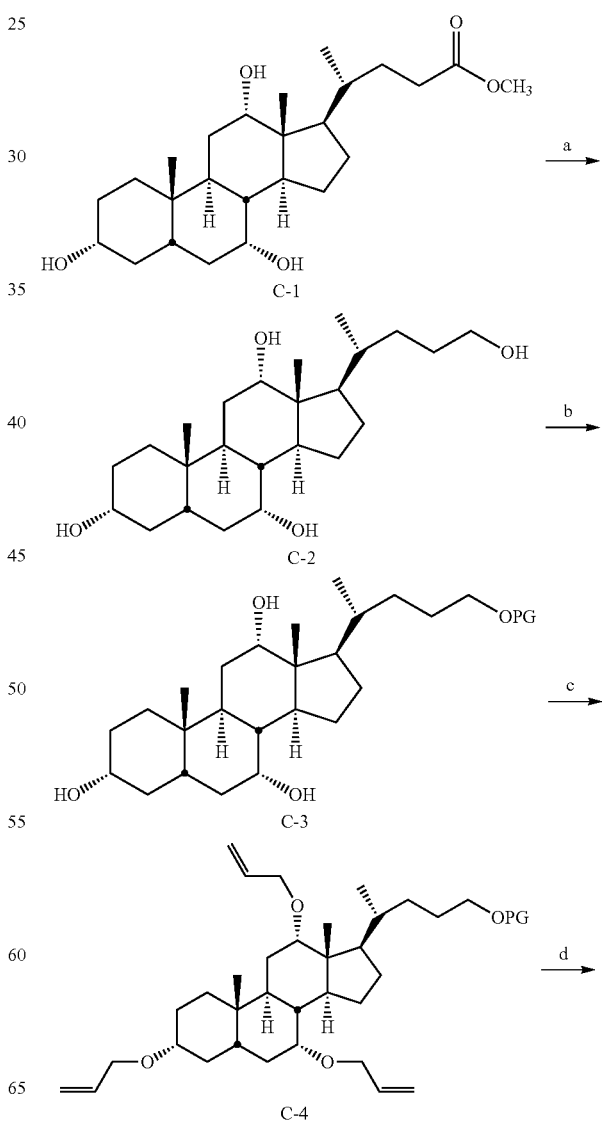

-continued

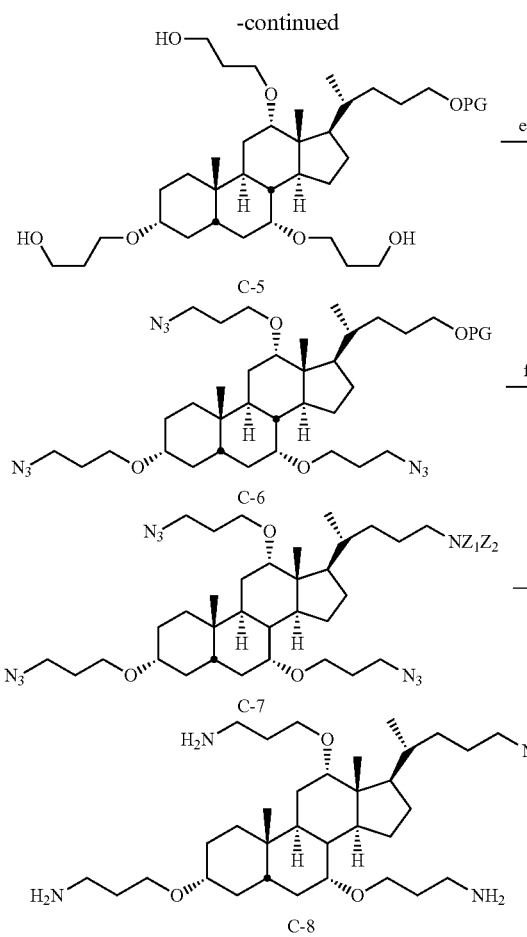

Reagents: (a) LiAlH$_4$, THF, (b) PG, Et$_3$N, DMF, (c) allyl-bromide, NaH, THF, (d) O$_3$, CH$_2$Cl$_2$, MeOH; Me$_2$S, NaBH$_4$, (e) MsCl, CH$_2$Cl$_2$, Et$_3$N; NaN$_3$, DMSO, (f) Deprotection; MsCl, CH$_2$Cl$_2$, Et$_3$N; HNZ$_1$Z$_2$, (g) LiALH$_4$, THF.

As shown above, compound C-1 is converted to the tetra-ol, compound C-2, using a reducing reagent such as lithium aluminum hydride. Treatment of C-2 with a protecting group ("PG") reagent selectively protects the primary alcohol providing compound C-3. A variety of alcohol protecting groups may be used for this transformation. See, e.g., T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973. Subsequent treatment of C-3 with allylbromide provides the allyl-ether functionalized compound C-4. Treatment of C-4 with ozone and subsequent reduction provides tri-ol C-5. C-5 is then treated with a reagent to create an oxygen-containing leaving group, such as methane sulfonyl chloride ("MsCl"), which is subsequently displaced upon treatment with nucleophilic azide resulting in the formation of C-6. The protection alcohol functionality of C-6 is deprotected using standard conditions and treated with a leaving group reagent as described above. The leaving group is then displaced by treatment with an optionally substituted alkyl amine to provide C-7. To facilitate nucleophilic displacement of the meslate leaving group, HNZ$_1$Z$_2$ may optionally be converted to an anion prior to displacement. C-7 is then subjected to reduction, using standard conditions, to reduce the azido functional groups to amines, resulting in C-8. A skilled artisan will readily appreciate that this general synthetic scheme can be modified to prepare the CSA compounds described herein, including CSA compounds with substituents and functional groups that are different from those generally described above. Furthermore, various nucleophiles such as HNZ$_1$Z$_2$ are either commercially available or readily prepared using known synthetic protocols from commercially available starting materials.

Scheme 2: Ester-Containing CSA Compounds

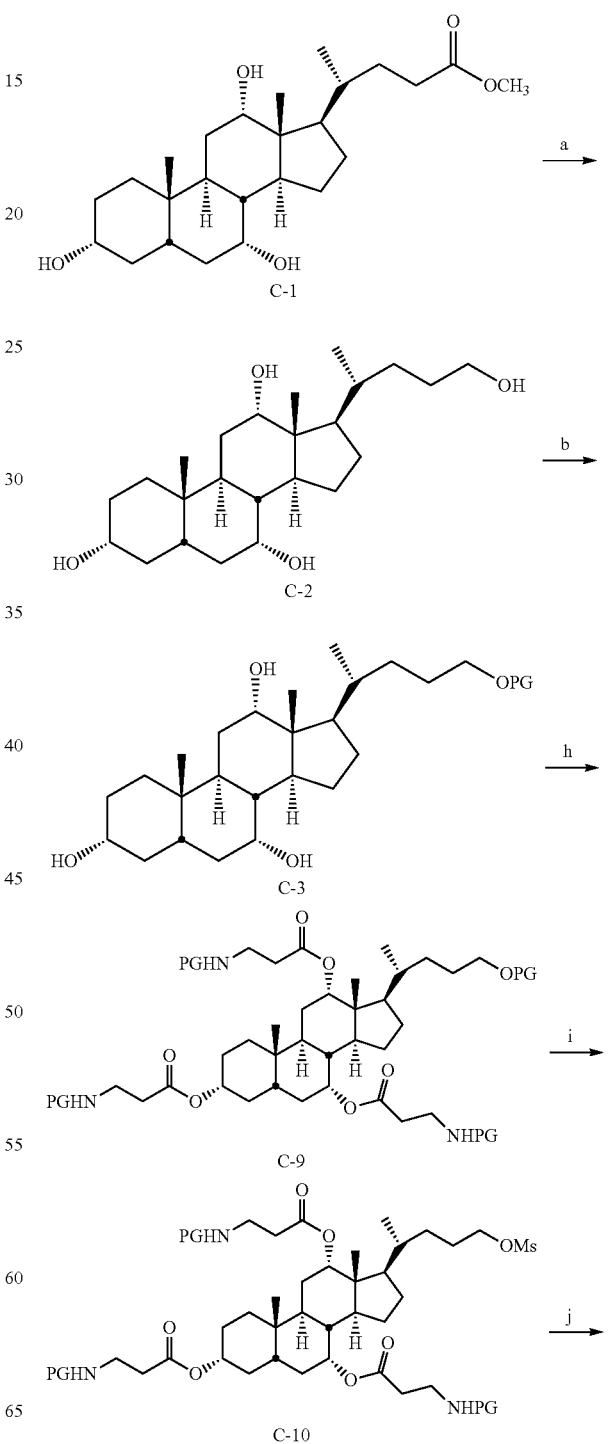

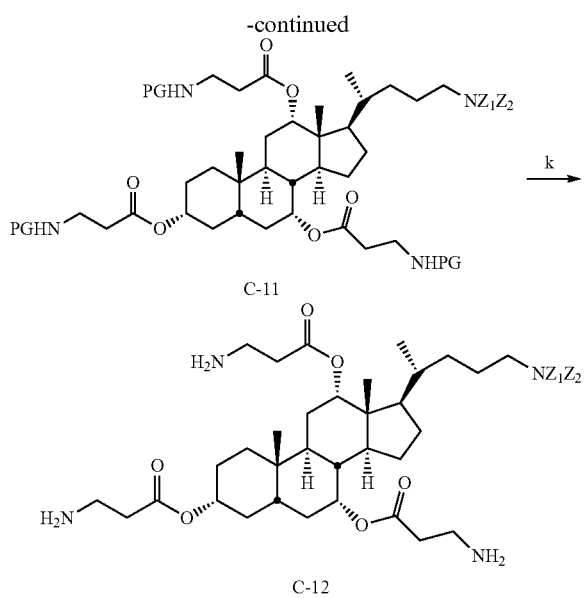

Reagents: (a) LiAlH$_4$, THF, (b) PG, Et$_3$N, DMF, (h) 3-PG-aminopropanoic acid, dicyclohexylcarbodiimide, N-hydroxysuccinimide, CH$_2$Cl$_2$, MeOH, (i) Deprotection; MsCl, CH$_2$Cl$_2$, Et$_3$N, (j) R—NH$_2$, CH$_2$Cl$_2$, Et$_3$N, (k) Deprotection.

As shown above, compound C-1 is converted to the tetra-ol, compound C-2, using a reducing reagent such as lithium aluminum hydride. Treatment of C-2 with a protecting group ("PG") reagent selectively protects the primary alcohol providing compound C-3. A variety of alcohol protecting groups may be used for this transformation. See, e.g., T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973. Compound C-3 is subsequently treated with esterification reagents [such as dicyclohexylcarbodiimide and N-hydroxysuccinimide, followed by 3-PG-aminopropanoic acid (the protected amine derivative of 3-aminopropanoic acid)] to provide compound C-9. Compound C-9 is deprotected using standard conditions and treated with a reagent to form a suitable leaving group (e.g. mesyl chloride) as described above, to provide C-10. Treatment of C-10 with an optionally substituted alkyl amine provides compound C-11, which is subjected to standard amine-deprotection conditions to provide CSA C-12. To facilitate nucleophilic displacement of the meslate leaving group, HNZ$_1$Z$_2$ may optionally be converted to an anion prior to displacement. A skilled artisan will readily appreciate that this general synthetic scheme can be modified to prepare the CSAs described herein, including CSAs with substituents and functional groups that are different from those generally described above. Furthermore, various nucleophiles such as HNZ$_1$Z$_2$ are either commercially available or readily prepared using known synthetic protocols from commercially available starting materials.

Non-limiting examples of CSA compounds described in the present application are generally illustrated in the table below. A skilled artisan will readily understand, in view of the present disclosure, that these CSAs can be prepared according to Schemes 1 or 2 above, or minor variations that are within ordinary skill in the art.

CSA Structure

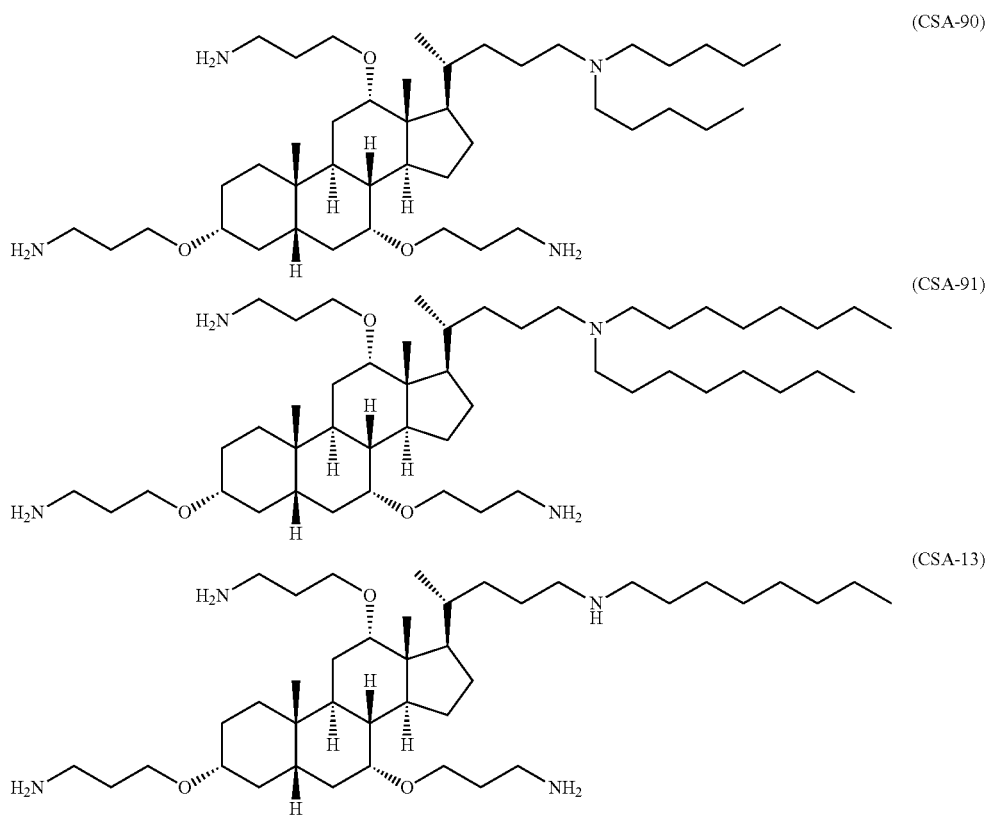

Using the above-described processes and procedures, additional CSA compounds generally and specifically described herein are synthesized and evaluated for their relative therapeutic efficacy. In some embodiments, the CSA compound is not CSA-13.

Compounds of the invention and precursors to the compounds according to the invention are available commercially, e.g., from Sigma-Aldrich Co., St. Louis; Mo.; and Research Plus, Inc., Manasquan, N.J. Other compounds according to the invention can be synthesized according to methods disclosed herein and in the art.

In some embodiments defined, all technical and scientific terms used herein have the same meaning as commonly understood by one of ordinary skill in the art to which this invention belongs. Although methods and materials similar or equivalent to those described herein can be used in the practice or study of the present invention, suitable methods and materials are described herein.

All of the features disclosed herein may be combined in any combination. Each feature disclosed in the specification may be replaced by an alternative feature serving a same, equivalent, or similar purpose. In some embodiments, disclosed features (e.g., compound structures) are an example of a genus of equivalent or similar features. All applications, publications, patents and other references, GenBank citations and ATCC citations cited herein are incorporated by reference in their entirety. In case of conflict, the specification, including definitions, will control.

As used herein, all numerical values or numerical ranges include integers within such ranges and fractions of the values or the integers within ranges unless the context clearly indicates otherwise. Thus, to illustrate, reference to a range of 90-100%, includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of 0-72 hrs, includes 1, 2, 3, 4, 5, 6, 7 hrs, etc., as well as 1, 2, 3, 4, 5, 6, 7 minutes, etc., and so forth. Reference to a range of doses, such as 0.1-1 µg/kg, 1-10 µg/kg, 10-25 µg/kg, 25-50 µg/kg, 50-100 µg/kg, 100-500 µg/kg, 500-1,000 µg/kg, 1-5 mg/kg, 5-10 mg/kg, 10-20 mg/kg, 20-50 mg/kg, 50-100 mg/kg, 100-250 mg/kg, 250-500 mg/kg, includes 0.11-0.9 µg/kg, 2-9 µg/kg, 11.5-24.5 µg/kg, 26-49 µg/kg, 55-90 µg/kg, 125-400 µg/kg, 750-800 µg/kg, 1.1-4.9 mg/kg, 6-9 mg/kg, 11.5-19.5 mg/kg, 21-49 mg/kg, 55-90 mg/kg, 125-200 mg/kg, 275.5-450.1 mg/kg, etc. A series of ranges, for example, 1-10 µg/kg, 10-25 µg/kg, 25-50 µg/kg, 50-100 µg/kg, 100-500 µg/kg, 500-1,000 µg/kg, 1-5 mg/kg, 5-10 mg/kg, 10-20 mg/kg, 20-50 mg/kg, 50-100 mg/kg, 100-250 mg/kg, 250-500 mg/kg, includes 1-25 µg/kg, 10-25 µg/kg, 25-100 µg/kg, 100-1,000 µg/kg, 1-10 mg/kg, 1-20 mg/kg etc.

A number of embodiments of the invention have been described. Nevertheless, one skilled in the art, without departing from the spirit and scope of the invention, can make various changes and modifications of the invention to adapt it to various usages and conditions. For example, salts, esters, ethers and amides of invention compounds disclosed herein are within the scope of this invention. Accordingly, the following examples are intended to illustrate but not limit the scope of invention described in the claims.

EXAMPLES

Anti-Infective Activities

Representative Procedure for Measuring MIC Values: A suspension is prepared of bacteria containing ~$10^6$ CFU (colony forming units)/mL from a culture incubated in TSB at 37° C. for 24 hours. Aliquots of 1 mL of the suspension are added to test tubes containing 1 mL TSB and incrementally varied concentrations of CSA compound. The samples are subjected to stationary incubation at 37° C. for 24 hours. Sample turbidity is determined by measuring absorption at 760 nm (HP 8453 UV-Visible Chemstation, Hewlett Packard). Additionally, an alliquot from each of the samples showing no measurable turbidity is subcultured on TSA plates (alliquots were diluted to provide fewer than 300 CFU). Colonies that grow on the subculture after overnight incubation are counted and the number of CFU/mL in the samples is calculated. The calculated values are compared to the number of CFU/mL in the original inoculum. MIC values are determined as the concentrations of the studied compounds at which the number of CFU/mL remained constant or decreased after incubation for 24 hours. CSA compounds were screened against methicillin-resistant *S. aureus* (MRSA) and tobramycin-resistant *P. aeruginosa* (TRPA). Representative data for CSA-90 and CSA-91 is provided in Table 1 below:

TABLE 1

| | MIC Values (µg/mL) | |
|---|---|---|
| Ceragenin | S. aureus (MRSA) | P. aeruginosa (TRPA) |
| CSA-90 | 0.6 | 3.0 |
| CSA-91 | 5.0 | 6.0 |

Ceragenins such as CSA-90 and CSA-91 are also known to be effective anti-viral agents (See U.S. Pat. No. 7,754,705).

Mammalian Ectopic Bone Formation Model

Using a mouse model, 10 µg rhBMP-2 was delivered via a Medronic absorbable collagen sponge (ACS). The effects of the addition of 25 µg and 250 µg ceragenin (CSA-90) were tested as was 250 µg ceragenin (CSA-90) dosed in the absence of rhBMP-2. Bone formation was examined by XR (Faxitron) and quantified by microCT (Skyscan 1174). Bone nodules were also examined by histology. Scanning data confirmed increases in bone volume with the addition of the ceragenin (See FIG. 1).

Figure 2:
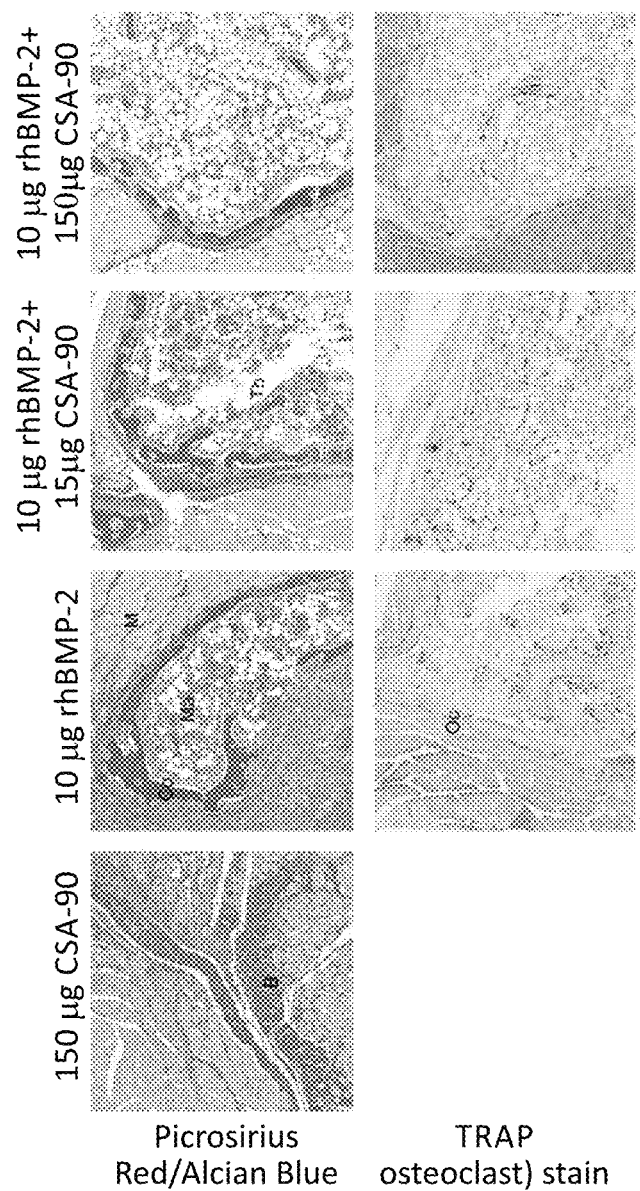
FIG. 2 includes photographs of microscope slides showing none nodule histology.

As FIG. 1 illustrates for the ectopic bone formation model, rhBMP-2 induced bone nodules as previously reported. Mean bone volume was significantly increased with the addition of both 25 µg CSA-90 (P=0.02) and 250 µg CSA-90 (P<0.01). The 250 µg CSA-90+rhBMP-2 treatment group showed a mean increase in bone volume of 3.2 fold by microCT over rhBMP-2 alone. Histological assessment showed no significant decrease in osteoclast number resulting from CSA-90 treatment, and the assessment showed a cortical shell and pseudo marrow space for rhBMP-2 treated groups and evidence of localized tissue mineralization with CSA-90 treatment alone (FIG. 2). These data suggest that CSA-90 was promoting bone anabolism rather than suppressing bone resorption.

Mammalian Open Fracture Model:

A mammalian open fracture model was conducted using rats (n=42, n=41 after anesthesia recovery) with and without bacteria inoculation, based on the gap healing model of Chen et al. (J Bone Joint Surg Am. 88-A:1510-23, 2006). In this model, infection was initiated by delivery of $10^4$ CFU of pathogenic *Staphlococcus aureus* in ACS at the time of surgery. Pilot work (n=10 rats) found that a bacterial load of $10^4$ led to non-union required euthanasia before 3 weeks.

Animals received treatment with 10 µg rhBMP-2 and/or 250 µg CSA-90 co-delivered via the ACS implant. The group design is shown in Table 2.

TABLE 2

| Group | Procedure | Treatment | N |
|---|---|---|---|
| 1 | Open fracture | None | 6 |
| 2 | Open fracture | 10 µg rhBMP-2 | 6 |
| 3 | Open fracture | 250 µg CSA-90 | 6 |
| 4 | Open fracture | 250 µg CSA-90 + 10 µg rhBMP-2 | 6 |
| 5 | Open fracture | $10^4$ cfu Staph | 3 |
| 6 | Open fracture | $10^4$ cfu Staph + 10 µg rhBMP-2 | 3 |
| 7 | Open fracture | $10^4$ cfu Staph + 250 µg CSA-90 | 6 |
| 8 | Open fracture | $10^4$ cfu Staph + 250 µg CSA-90 + 10 µg rhBMP-2 | 6 |

The primary outcome measure was the number of animals culled with infected fractures. Animal health and radiographic bone healing were monitored by an experienced veterinarian in a blinded fashion to inoculation or treatment. Animals diagnosed as having progressively deteriorating condition with XRs showing evidence of infection were culled and infection confirmed by culture swab post-mortem. Secondary outcome measures included union at 3 weeks and 6 weeks (excluding pin-slippage), and bone callus microCT measures at 6 weeks.

Figure 3:
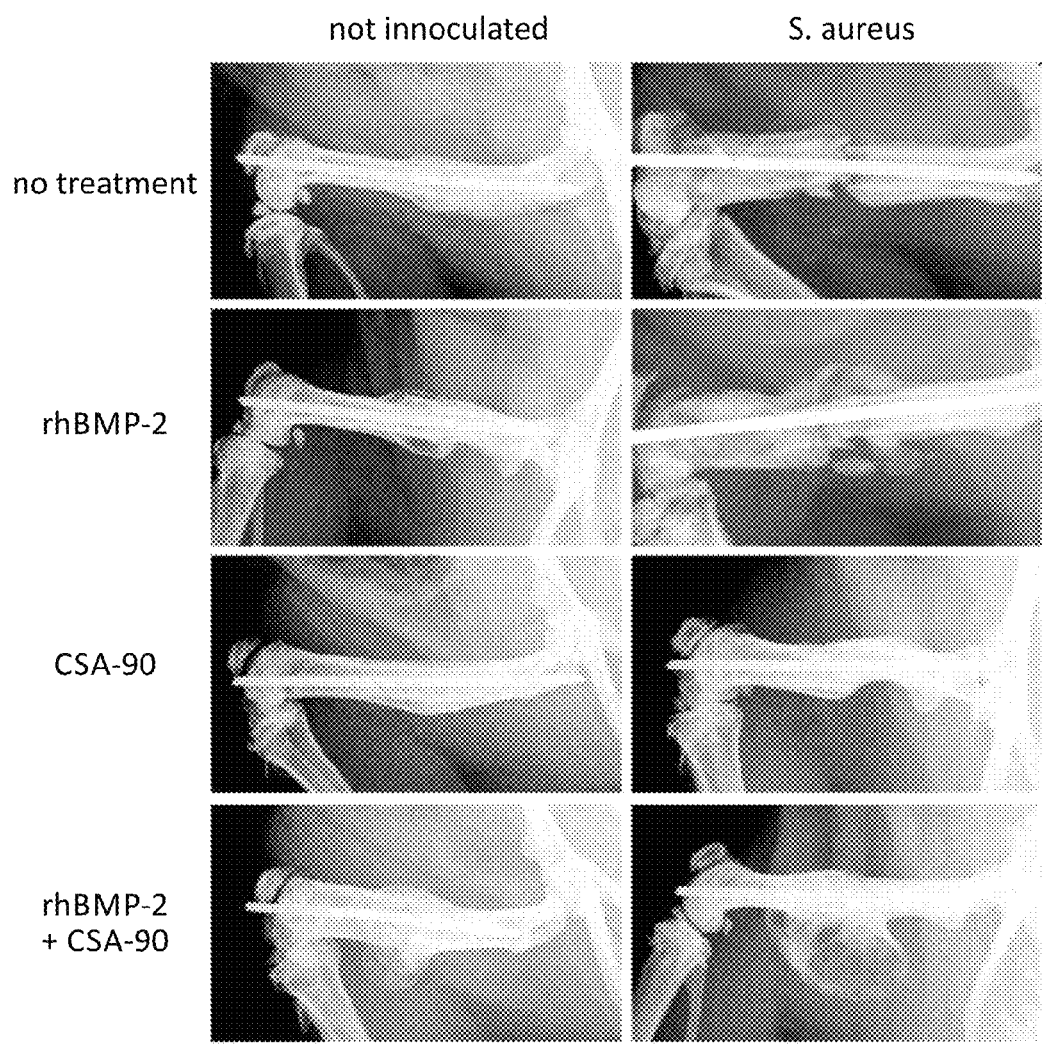
FIG. 3 includes representative X-ray images of fractured femora.
Figure 4B:
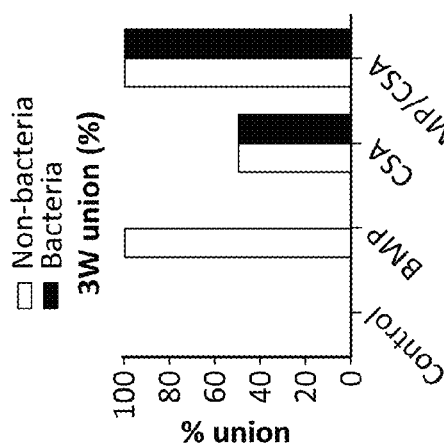
FIGS. 4A-4C are graphical representations of infection rate and pin slip rate.
Figure 4C:
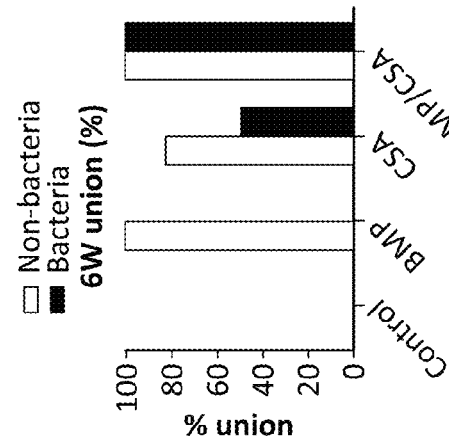
Figure 4A:
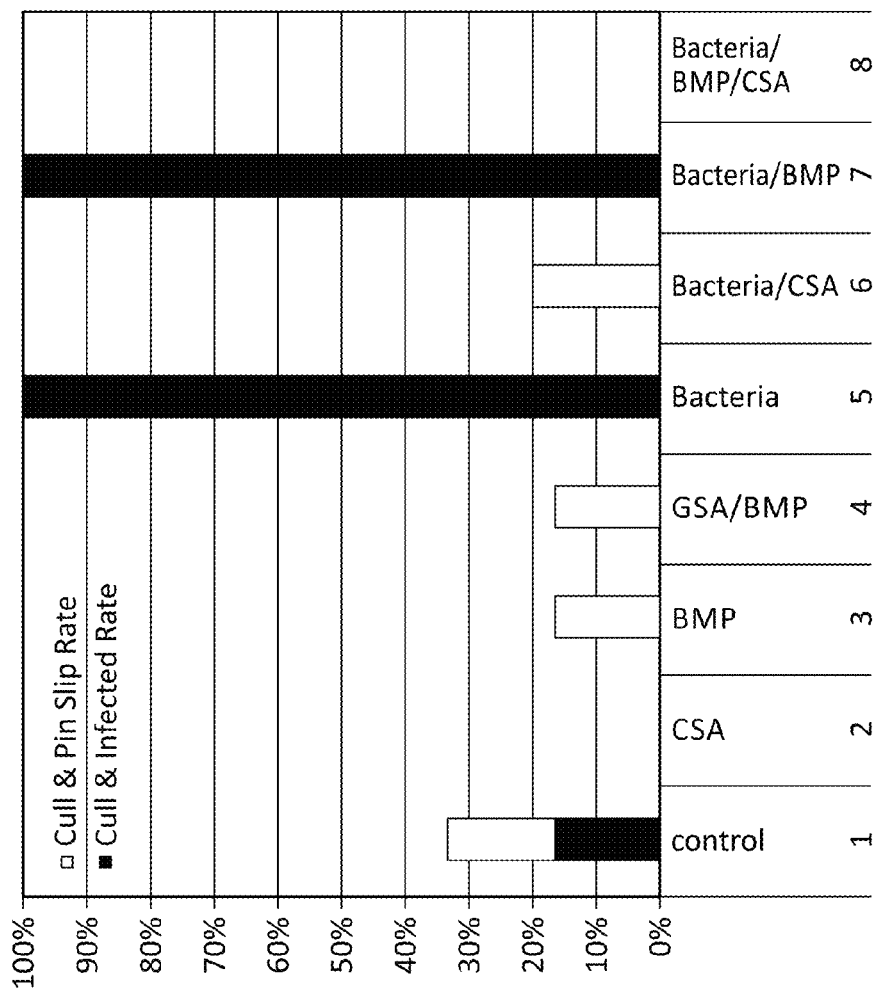
Figure 5A:
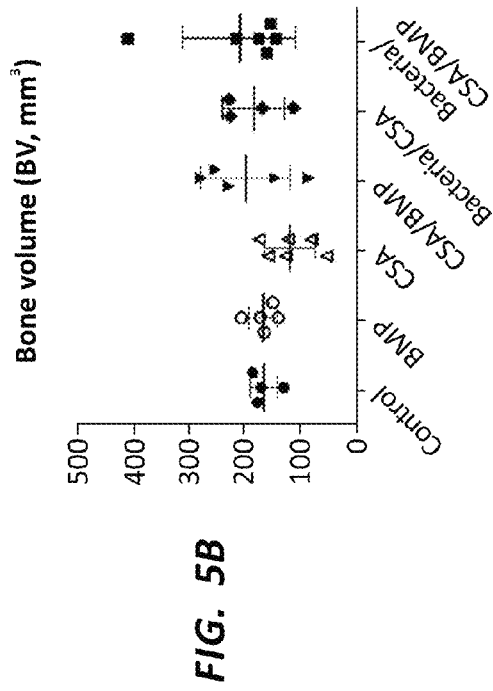
FIGS. 5A-5D are graphs showing MicroCT results assessing bone and tissue volume parameters of the bone fracture callus.
Figure 5B:
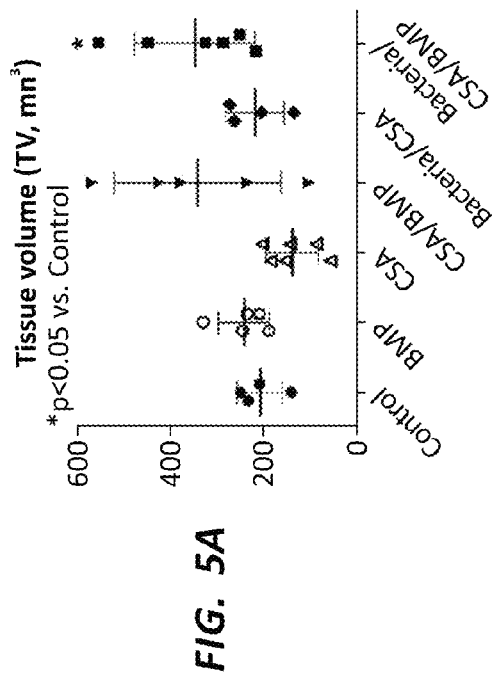
Figure 5C:
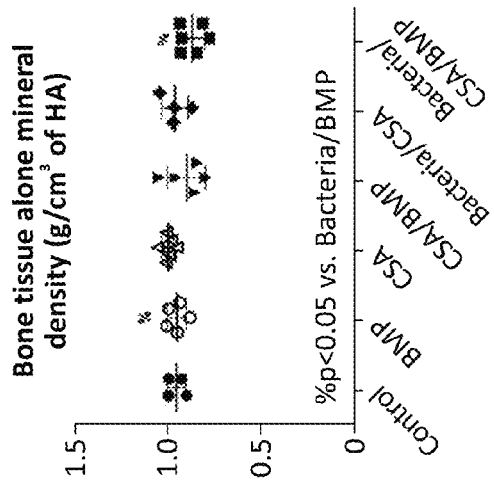
Figure 5D:
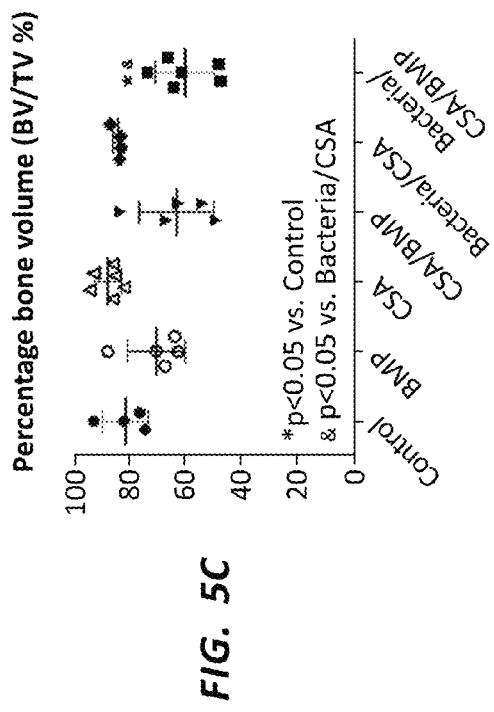

In the open fracture model, inoculation with *S. aureus* led to all animals being culled with infections at ~day 17 when given no treatment or dosed with rhBMP-2 (n=3 per group). In the inoculated groups, with CSA-90 or CSA-90+rhBMP-2 resulted in no infected culls (n=6 per group), with one animal from the CSA-90 group culled with a pin slip (no infection seen in culture) (FIG. 3). At 3 weeks no unions were seen in the control non-inoculated fractures. In contrast, the union rate was ~50% in the CSA-90 treated groups and 100% in the rhBMP-2 group (no *S. aureus*) and 100% in the CSA-90+rhBMP-2 groups. By 6 weeks 50% of the control open fractures and the union rate in the CSA-90 group had also increased but not to 100% (FIGS. 4A-4C). MicroCT analysis showed an a significant increase in tissue volume of the callus in the CSA-90+rhBMP-2 group compared to controls at 6 weeks, although callus remodeling was advanced in all groups by this time point (FIGS. 5A-5D). A table providing the infection and pin slips in culled animals is provided in Table 3.

TABLE 3

| Group | Group ID | Infected Cull Rate | Pin Slip Cull Rate | # Infected Culls | # Pin Slips |
|---|---|---|---|---|---|
| 1 | Control | 17% | 17% | 1/6 | 1/6 |
| 2 | CSA | 0% | 0% | 0/6 | 0/6 |
| 3 | BMP | 0% | 17% | 0/6 | 1/6 |
| 4 | CSA/BMP | 0% | 17% | 0/6 | 1/6 |
| 5 | Bacteria | 100% | 0% | 3/3 | 0/3 |
| 6 | Bacteria/CSA | 0% | 20% | 0/5 | 1/5 |
| 7 | Bacteria/BMP | 100% | 0% | 3/3 | 0/3 |
| 8 | Bacteria/BMP/CSA | 0% | 0% | 0/6 | 0/6 |

Data Summation

These data show that CSA compounds dosed at the time of operation can have a prophylactic effect and prevent the development of a persistent infection that would otherwise lead to non-union. Moreover, the CSA compounds represent a new class of antibiotics and their use would not contribute to the resistance to other antibiotics. Few models of orthopedic infection exist in the literature and these studies demonstrate the disclosed model is reproducible and able to test antibiotic efficacy. These data also suggest that in addition to its antibiotic activity, CSA compounds are able to promote bone healing. In the ectopic bone formation model the representative compound showed synergy with rhBMP-2 to increase bone volume. In the fracture model the representative compound led to an increase in early union at 3 weeks. While rhBMP-2 led to greater and more rapid increases in union, rhBMP-2 alone in the presence of bacteria did not promote union in this model. Synergy of rhBMP-2 was also seen with the representative compound in terms of callus tissue volume. Indeed, the data indicate that the representative compound completely prevented facture repair failure resulting from bacterial inoculation. Furthermore, union data at 3 weeks shows evidence of improved union with the representative compound alone, with and without bacterial inoculation over non-inoculated and untreated controls. These data support the concept of CSA compounds as dual-function orthopedic agent; the representative compound prevented infection and promoted bone formation and repair, alone and in combination with rhBMP-2.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

The invention claimed is:

1. A method of reducing the likelihood of a bone infection in a subject having a broken bone, a bone implant, osteoporosis, or osteoarthritis while concurrently promoting osteogenesis in a subject in need thereof, the method comprising:
administering to the subject in need thereof a CSA compound of Formula (I), or a pharmaceutically acceptable salt thereof:

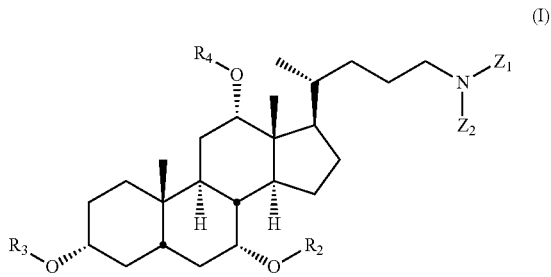

(I)

wherein $Z_1$ and $Z_2$ are independently selected from the group consisting of optionally substituted alkyl; optionally substituted alkenyl; and optionally substituted alkynyl, or H, with the proviso that $Z_1$ and $Z_2$ are not both H, wherein $R_2$, $R_3$, and $R_4$, are independently selected from the group consisting of optionally substituted protected or unprotected amino-$C_a$-alkyl; optionally substituted protected or unprotected amino-$C_a$-alkylcarbonyl; and optionally substituted protected or unprotected amino-$C_a$-alkylthiocarbonyl, and wherein a is 2-5; and co-administering a bone growth factor to the subject, wherein co-administering the bone growth factor and the CSA compound potentiates a synergistic effect in promoting osteogenesis and reduces the likelihood of a bone infection associated with the broken bone, the bone implant, osteoporosis, or osteoarthritis in the subject.

2. The method of claim 1, wherein the subject is a mammal.

3. The method of claim 1, wherein the subject is a human.

4. The method of claim 1, wherein $Z_1$ and $Z_2$ are optionally substituted alkyl.

5. The method of claim 1, wherein $Z_1$ and $Z_2$ are independently selected from the group consisting of optionally substituted $C_1$-$C_{20}$-alkyl; optionally substituted $C_3$-$C_{20}$-alkenyl; and optionally substituted $C_3$-$C_{20}$-alkynyl.

6. The method of claim 1, wherein $Z_1$ and $Z_2$ are independently selected from the group consisting of optionally substituted $C_3$-$C_{10}$-alkyl; optionally substituted $C_3$-$C_{10}$-alkenyl; and optionally substituted $C_3$-$C_{10}$-alkynyl.

7. The method of claim 1, wherein $Z_1$ and $Z_2$ are independently selected from the group consisting of optionally substituted $C_5$-$C_8$-alkyl; optionally substituted $C_3$-$C_{10}$-alkenyl; and optionally substituted $C_5$-$C_8$-alkynyl.

8. The method of claim 1, wherein $Z_1$ and $Z_2$ are optionally substituted $C_5$-$C_8$-alkyl.

9. The method of claim 1, wherein $Z_1$ and $Z_2$ are unsubstituted $C_5$-$C_8$-alkyl.

10. The method of claim 1, wherein $R_2$, $R_3$, and $R_4$, are amino-$C_a$-alkyl or amino-$C_a$-alkylcarbonyl.

11. The method of claim 1, wherein $R_2$, $R_3$, and $R_4$, are amino-$C_a$-alkyl.

12. The method of claim 1, wherein $R_2$, $R_3$, and $R_4$, are amino-$C_a$-alkylcarbonyl.

13. The method of claim 10, wherein a is selected from 2, 3, 4, or 5.

14. The method of claim 1, wherein the protected amino-$C_a$-alkyl and the protected amino-$C_a$-alkylcarbonyl are protected with a group independently selected from Fmoc, Boc, allyl, acetyl, benzyl, or CBz.

15. The method of claim 1, wherein $R_2$, $R_3$, and $R_4$, are independently selected from the group consisting of carbamate protected or unprotected amino-$C_a$-alkyl and carbamate protected or unprotected amino-$C_a$-alkylcarbonyl.

16. The method of claim 1, wherein $R_2$, $R_3$, and $R_4$, are independently selected from the group consisting of Fmoc protected or unprotected amino-$C_a$-alkyl and Fmoc protected or unprotected amino-$C_a$-alkylcarbonyl.

17. The method of claim 1, wherein $R_2$, $R_3$, and $R_4$, are independently selected from the group consisting of Boc protected or unprotected amino-$C_a$-alkyl and Boc protected or unprotected amino-$C_a$-alkylcarbonyl.

18. The method of claim 1, wherein the compound of Formula (I) is:

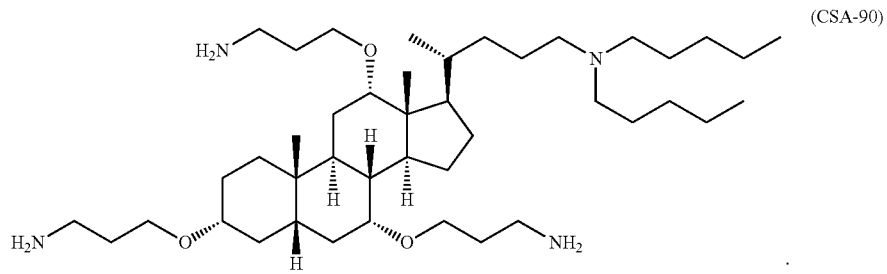

(CSA-90)

19. The method of claim 1, wherein the compound is not substituted.

20. The method of claim 1, wherein the pharmaceutically acceptable salt is a hydrochloride salt.

21. The method of claim 1, wherein the growth factor comprises a bone morphogenetic protein.

22. A method of treating osteoarthritis in a subject in need thereof, comprising:

administering to the subject in need thereof a CSA compound of Formula (I), or a pharmaceutically acceptable salt thereof:

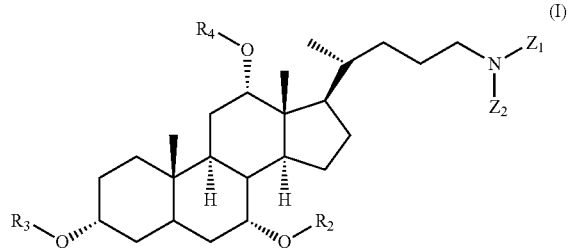

(I)

wherein $Z_1$ and $Z_2$ are independently selected from the group consisting of optionally substituted alkyl; optionally substituted alkenyl; and optionally substituted alkynyl, or H, with the proviso that $Z_1$ and $Z_2$ are not both H, wherein $R_2$, $R_3$, and $R_4$, are independently selected from the group consisting of optionally substituted protected or unprotected amino-Ca-alkyl; optionally substituted protected or unprotected amino-Ca-alkylcarbonyl; and optionally substituted protected or unprotected amino-Ca-alkylthiocarbonyl, and wherein a is 2-5.

23. A method of treating a degenerative bone condition or a bone condition caused by a microbial infection while concurrently promoting osteogenesis in a subject in need thereof, comprising:

providing a CSA-90 compound of Formula (I), or a pharmaceutically acceptable salt thereof, and a recombinant bone morphogenetic protein on a drug delivery vehicle:

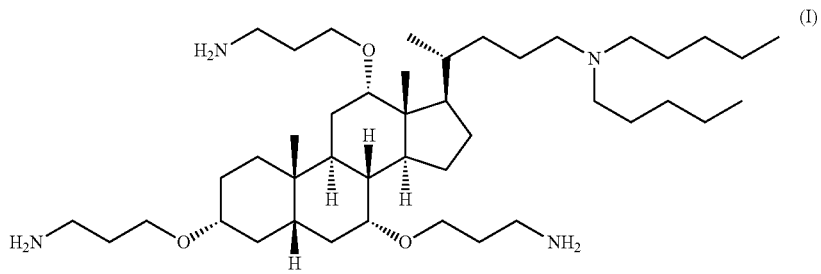

(I)

wherein $Z_1$ and $Z_2$ are independently selected from the group consisting of optionally substituted alkyl; optionally substituted alkenyl; and optionally substituted alkynyl, or H, with the proviso that $Z_1$ and $Z_2$ are not both H, wherein $R_2$, $R_3$, and $R_4$, are independently selected from the group consisting of optionally substituted protected or unprotected amino-$C_a$-alkyl; optionally substituted protected or unprotected amino-$C_a$-alkylcarbonyl; and optionally substituted protected or unprotected amino-$C_a$-alkylthiocarbonyl, and wherein a is 2-5; and administering the drug delivery vehicle to a site of the degenerative bone condition or to a site of the bone condition caused by the microbial infection to synergistically promote osteogenesis and to prevent or treat the microbial infection.

24. The method of claim 22, further comprising co-administering a bone growth factor to the subject, wherein co-administering the bone growth factor and the CSA compound potentiates a synergistic effect in promoting osteogenesis in the subject.

25. The method of claim 23, wherein between about 25 μg to about 250 μg of the CSA compound is provided on the drug delivery vehicle.

26. The method of claim 23, wherein at least about 10 μg of the recombinant bone morphogenetic protein is provided on the drug delivery vehicle.

27. The method of claim 25, wherein the recombinant bone morphogenetic protein comprises one or more of BMP-2, BMP-3, BMP-4, BMP-5, BMP-5, or BMP-7.

28. The method of claim 26, wherein the recombinant bone morphogenetic protein comprises BMP-2.

* * * * *

UNITED STATES PATENT AND TRADEMARK OFFICE
CERTIFICATE OF CORRECTION

PATENT NO. : 9,931,350 B2
APPLICATION NO. : 14/645040
DATED : April 3, 2018
INVENTOR(S) : Savage et al.

It is certified that error appears in the above-identified patent and that said Letters Patent is hereby corrected as shown below:

On the Title Page

Item (56), Page 3, OTHER PUBLICATIONS, Column 1, Line 17-20:
Change "Fritsch et al, "In Vitro Activity of Nine Developmental Cationic Steroid Compounds (Ceragenins) against Clnical Isolates of Clostridium difficile", The 46th Interscience Conference on Anti-microbial Agents and Chemotherapy, Sep. 27, 2006, pp. 1-1." to –Fritsch et al, "In Vitro Activity of Nine Developmental Cationic Steroid Compounds (Ceragenins) against Clinical Isolates of Clostridium difficile", The 46th Interscience Conference on Anti-microbial Agents and Chemotherapy, Sep. 27, 2006, pp. 1-1.–

In the Specification

Column 5
Line 36, change "none" to –known–

Column 10
Line 13, change "atom" to –atoms–
Line 29, change "atom" to –atoms–

Column 11
Line 12, change "atom" to –atoms–

Column 14
Line 62, change "understand" to –understood–

Column 16
Line 14, change "sat" to –salt–
Line 53, change "have a" to –have–

Signed and Sealed this
Thirty-first Day of July, 2018

Andrei Iancu
*Director of the United States Patent and Trademark Office*

Column 29
Line 29, change "containes" to –contains–
Lines 40-41, change "comprIn some embodiments" to –comprises–
Line 58, change "comprIn some embodiments" to –comprises–

Column 31
Line 39, change "otherwIn some embodiments" to –otherwise–
Line 58, change "din some embodimentsases" to –diseases–

Column 32
Line 32, change "tablet" to –tablets–

Column 33
Line 52, remove [or]

Column 41
Line 43, remove [an]